US011103602B2

(12) United States Patent
Degrado et al.

(10) Patent No.: US 11,103,602 B2
(45) Date of Patent: Aug. 31, 2021

(54) PET IMAGING OF ZINC TRANSPORT

(71) Applicant: Mayo Foundation for Medical Education and Research, Rochester, MN (US)

(72) Inventors: Timothy R. Degrado, Rochester, MN (US); Mukesh K. Pandey, Rochester, MN (US); Hendrik Petrus Engelbrecht, Rochester, MN (US); Val J. Lowe, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 16/355,335

(22) Filed: Mar. 15, 2019

(65) Prior Publication Data
US 2019/0209716 A1    Jul. 11, 2019

Related U.S. Application Data

(62) Division of application No. 14/902,744, filed as application No. PCT/US2014/045960 on Jul. 9, 2014, now Pat. No. 10,279,054.

(60) Provisional application No. 61/844,222, filed on Jul. 9, 2013.

(51) Int. Cl.
*A61K 51/04* (2006.01)
*C07B 59/00* (2006.01)

(52) U.S. Cl.
CPC ...... *A61K 51/0402* (2013.01); *A61K 51/0478* (2013.01); *C07B 59/001* (2013.01)

(58) Field of Classification Search
CPC ................................ A61K 51/00; C07B 59/00
See application file for complete search history.

(56) References Cited

U.S. PATENT DOCUMENTS

| 6,222,896 | B1 | 4/2001 | Jia | |
| 8,586,595 | B2* | 11/2013 | Low | A61K 51/0497 514/262.1 |
| 9,028,587 | B2 | 5/2015 | Le | |
| 2004/0265847 | A1* | 12/2004 | Masters | G01N 33/6896 435/6.14 |
| 2007/0040115 | A1 | 2/2007 | Publicover et al. | |
| 2008/0090297 | A1* | 4/2008 | Richards | A61K 49/0004 436/80 |
| 2010/0322854 | A1 | 12/2010 | Low | |

FOREIGN PATENT DOCUMENTS

WO    2004064869 A2    8/2004

OTHER PUBLICATIONS

Luis De Leon-Rodriguezetal. Imaging free zinc levels in vivo—what can be learned, Inorganica Chim Acta, 393, 12-23. (Year: 2012).*
Suzanne V. Smith et al. Production and Selection of Metal PET Radioisitopes for Molecular Imaging, Radioisotopes-Application in Bio-Medical Science. (Year: 2011).*
Sibrata K. Ghosh et al. A Novel Imaging Approach for Early Detection of Prostate Cancer Based on Endogenous Zinc Sensing, Cancer Res; 70(15), 6119-6127. (Year: 2010).*
Guerra Gomez Francisco Lazaro, Development of Metal-Based Radiopharmaceuticals for Positron Emission Tomography Imaging: Production of Zinc-63 and Molecular Design for Gallium-68 Labeled Probes, Chapter 1, pp. 13-27. (Year: 2013).*
Adlard, et al., Rapid Restoration of Cognition in Alzheimer's Transgenic Mice with 8-Hydroxy Quinoline Analogs Is Associated with Decreased Interstitial Aβ, Neuron, 2008, 59:43-55.
Adlard, et al., Metals and Alzheimer's Disease, Journal of Alzheimer's Disease, 2006, 10:145-163.
Adlard, et al., Metal Chaperones: A Holistic Approach to the Treatment of Alzheimer's Disease, Frontiers in Psychiatry, 2012, vol. 3, Article 15, pp. 1-5.
Alam, et al., Cellular Mechanisms of Zinc Dysregulation: A Perspective on Zinc Homeostasis as an Etiological Factor in the Development and Progression of Breast Cancer, Nutrients, 2012, 4:875-903.
Blindauer, et al., Structure, Properties, and Engineering of the Major Zinc Binding Site on Human Albumin, Journal of Biological Chemistry, 2009, 284(34):23116-23124.
Buxani-Rice, et al., Transport of Zinc-65 at the Blood-Brain Barrier During Short Cerebrovascular Perfusion in the Rat: Its Enhancement by Histidine, Journal of Neurochemistry, 1994, 62(2):665-672.
Chen, et al., Differential Sensitivity of Recombinant N-Methyl-D-Aspartate Receptor Subtypes to Zinc Inhibition, Molecular Pharmacology, 1997, 51:1015-1023.
Cohen-Kfir, et al., Zinc Inhibition of y-aminobutyric Acid Transporter 4 (GAT4) Reveals a Link Between Excitatory and Inhibitory Neurotransmission, PNAS, 2005, 102(17):6154-6159.
Costello, et al., Decreased Zinc and Downregulation of ZIP3 Zinc Uptake Transporter in the Development of Pancreatic Adenocarcinoma, Cancer Biology & Therapy, 2011, 12(4):297-303.

(Continued)

*Primary Examiner* — Michael G. Hartley
*Assistant Examiner* — Jagadishwar R Samala
(74) *Attorney, Agent, or Firm* — Quarles & Brady LLP

(57) ABSTRACT

A method for producing a solution including a positron emitting zinc cation of $^{63}$Zn, and the method comprises bombarding a solution target including $^{63}$Cu with high energy protons to produce a solution including a positron emitting zinc cation. A method for detecting or ruling out Alzheimer's disease in a patient comprises administering to a patient a detectable amount of a compound including a positron emitting zinc cation, wherein the zinc cation is targeted to β-amyloid in the patient, and acquiring an image to detect the presence or absence of β-amyloid in the patient. A method for detecting or ruling out cancer in a patient comprises administering to a patient a detectable amount of a compound including a positron emitting zinc cation, wherein the zinc cation is targeted to tissue in the patient; and acquiring an image using a medical imaging technique to detect zinc distribution in tissue in the patient.

14 Claims, 13 Drawing Sheets

(56) References Cited

OTHER PUBLICATIONS

Costello, et al., The Status of Zinc in the Development of Hepatocellular Cancer, Cancer Biology & Therapy, 2014, 15(4):353-360.
Craddock, et al., The Zinc Dyshomeostasis Hypothesis of Alzheimer's Disease, PLoS One, 2012, 7(3):e33552, pp. 1-16.
Deshpande, et al., A Role for Synaptic Zinc in Activity-Dependent Aβ Oligomer Formation and Accumulation at Excitatory Synapses, Journal of Neuroscience, 2009, 29(13):4004-4015.
Engelbrecht, et al., Production of Zn-63 via Solution Target and Biodistribution in Mice, J. Nucl. Med., 2013, 54 (Supplement 2):386, 2 pages.
Faux, et al., PBT2 Rapidly Improves Cognition in Alzheimer's Disease: Additional Phase II Analyses, Journal of Alzheimer's Disease, 2010, 20:509-516.
Frassinetti, et al., The Role of Zinc in Life: A Review, Journal of Environmental Pathology, Toxicology, and Oncology, 2006, 25(3):597-610.
Fujibayashi, et al., A Radiopharmaceutical for Pancreatic Exocrine Functional Diagnosis: 62Zn-EDDA Metabolism in Pancreas, International Journal of Nuclear Medicine and Biology, 1986, 12(6):447-451.
Gomez, et al., Production and Purification of the Positron Emitter Zinc-63, Journal of Labelled Compounds and Radiopharmaceuticals, 2012, 55:5-9.
Gur, et al., Determination of Hepatic Zinc Content in Chronic Liver Disease Due to Hepatitis B Virus, Hepato-Gastroenterology, 1998, 45(20):472-476.
Kanayama, et al., Multiracer Screening: Brain Delivery of Trace Elements by Eight Different Administration Methods, BioMetals, 2005, 18(6):553-565.
Kolenko, et al., Zinc and Zinc Transporters in Prostate Carcinogenesis, Nat. Rev. Urol, 2013, 10(4):219-226.
Lannfelt, et al., Safety, Efficacy, and Biomarker Findings of PBT2 in Targeting Aβ as a Modifying Therapy for Alzheimer's Disease: A Phase IIa, Double-Blind, Randomised, Placebo-Controlled Trial, Lancet Neurol., 2008, 7:779-786.
Laube, Potentiation of Inhibitory Glycinergic Neurotransmission by Zn2+: A Synergistic Interplay Between Presynaptic P2X2 and Postsynaptic Glycine Receptors, European Journal of Neuroscience, 2002, 16(6):1025-1036.
Li, Zinc and Insulin in Pancreatic Beta-Cells, Endocrine, 2014, 45(2):178-189.
Lu, et al., Albumin as a Zinc Carrier: Properties of Its High-Affinity Zinc-Binding Site, Biochem. Soc. Trans., 2008, 36:1317-1321.
Lyster, The Unit Dose Preparation of 63Zn-EDTA for Use in Nuclear Medicine, International Journal of Nuclear Medicine and Biology, 1974, 1(4):220-223.
Mathis, et al., Development of Positron Emission Tomography β-Amyloid Plaque Imaging Agents, Semin. Nucl. Med., 2012, 42(6):423-432.
Miao, et al., Zinc Homeostasis in the Metabolic Syndrome and Diabetes, Front. Med., 2013, 7(1):31-52.
Nutini, et al., Zinc Pre-Treatment Enhances NMDAR-Mediated Excitotoxicity in Cultured Cortical Neurons from SOD1-G93A Mouse, a Model of Amyotrophic Lateral Sclerosis, Neuropharmacology, 2011, 60:1200-1208.
Opazo, et al., Metalloenzyme-Like Activity of Alzheimer's Disease β-Amyloid, Journal of Biological Chemistry, 2002, 277(43):40302-40308.
Ostrowitzki, et al., Mechanism of Amyloid Removal in Patients With Alzheimer Disease Treated With Gantenerumab, Arch. Neurol., 2012, 69(2):198-207.
Pandey, et al., Production of 89Zr via the 89Y(p,n)89Zr Reaction in Aqueous Solution: Effect of Solution Composition on In-Target Chemistry, Nuclear Medicine and Biology, 2014, 41:309-316.
Pandey, et al., Cyclotron Production of 68Ga via the 68Zn(p,n)68Ga Reaction in Aqueous Solution, Am. J. Nucl. Vied. Mol. Imaging, 2014, 4(4):303-310.
Penny, Zinc Supplementation in Public Health, Annals of Nutrition & Metabolism, 2013, 62(Suppl. 1):31-42.
Pullen, et al., 65Zinc Uptake from Blood Into Brain and Other Tissues in the Rat, Neurochemical Research, 1990, 15(10):1003-1008.
Religa, et al., Elevated Cortical Zinc in Alzheimer Disease, Neurology, 2006, 67:69-75.
Rinne, et al., 11C-PiB PET Assessment of Change in Fibrillar Amyloid-β Load in Patients with Alzheimer's Disease Treated with Bapineuzumab: A Phase 2, Double-Blind, Placebo-Controlled, Ascending-Dose Study, Lancet Neurology, 2010, 9:363-372.
Stairs, Copper Dissolution in Nitric Acid, Journal of Chemical Education, 1990, 67(2):184.
Takeda, Movement of Zinc and Its Functional Significance in the Brain, Brain Research Reviews, 2000, 34 (3):137-148.
Tamano, et al., Preferential Uptake of Zinc, Manganese, and Rubidium in Rat Brain Tumor, Nuclear Medicine and Biology, 2002, 29(4):505-508.
Tibaduiza, et al., Zinc Transport Across an Endothelium Includes Vesicular Cotransport with Albumin, Journal of Cellular Physiology, 1996, 167(3):539-547.
Torosyan, et al., Neuronuclear Imaging in the Evaluation of Dementia and Mild Decline in Cognition, Semin. Nucl. Med., 2012, 42(6):415-422.
Watt, et al., The Role of Zinc in Alzheimer's Disease, International Journal of Alzheimer's Disease, 2011, vol. 2011, Article ID 971021, 10 pages.
Wu, Zinc Sulfate Could be a Potential Agent for the Treatment of Huntington's Disease Through Activating Central TrkB Signaling, CNS Spectr., 2010, 15(1):56-57.
PCT International Search Report and Written Opinion, PCT/US2014/045960, dated Dec. 19, 2014.

\* cited by examiner

PET IMAGING OF ZINC TRANSPORT

CROSS-REFERENCE TO RELATED APPLICATIONS

This application is a divisional application of U.S. patent application Ser. No. 14/902,744 filed Jan. 4, 2016, which is a 371 application of PCT/US14/45960, filed Jul. 9, 2014, which claims priority from U.S. Patent Application No. 61/841,222 filed Jul. 9, 2013.

STATEMENT REGARDING FEDERALLY SPONSORED RESEARCH

This invention was made with government support under SC0008947 awarded by Department of Energy. The government has certain rights in the invention.

BACKGROUND OF THE INVENTION

The field of the invention is positron emission tomography (PET) imaging. More particularly, the invention relates to PET imaging of $^{63}$Zn distribution in biological systems (including human) for noninvasive measurement of zinc transport and biodistribution.

Alzheimer's disease (AD) is the most common cause of dementia in the elderly, affecting more than 4 million people in the United States. However, the diagnosis and treatment of the disease have been hampered by the absence of reliable noninvasive markers for the underlying pathology. The most developed areas of molecular imaging of AD entails PET imaging of glucose metabolism using [$^{18}$F]FDG [Torosyan et al., Neuronuclear imaging in the evaluation of dementia and mild decline in cognition. *Semin Nucl Med.* 2012; 42(6):415-22] and β-amyloid (Aβ) plaque burden using [$^{11}$C]PiB [Mathis et al., Development of positron emission tomography β-amyloid plaque imaging agents. *Semin Nucl Med.* 2012 November; 42(6):423-32.] or similar probes that are brain penetrant and bind to Aβ plaques. These agents have provided valuable data on cortical brain metabolism and Aβ plaque burden but there is yet critical need for molecular imaging agents that get closer to AD pathophysiology. For example, ~60% of mild cognitive impairment (MCI) patients have levels of PiB retention similar to that seen in AD, and approximately 25% of cognitively normal elderly people in their seventies have measurable PiB retention, suggesting that Aβ plaque deposition in the brain is not alone sufficient to cause symptomatic AD [Rinne et al., $^{11}$C-PiB PET assessment of change in fibrillar amyloid-beta load in patients with Alzheimer's disease treated with bapineuzumab: A phase 2, double-blind, placebo controlled, ascending-dose study. *Lancet Neurol* 2010; 9:363-372; Ostrowitzki et al., Mechanism of amyloid removal in patients with Alzheimer disease treated with gantenerumab. *Arch Neurol* 2012; 69:198-207].

Abnormal metal (zinc, copper, and iron) homeostasis is implicated in the deposition of Aβ in AD [Adlard et al., Metal chaparones: a holistic approach to the treatment of Alzheimer's disease. *Frontiers Psychiatry* 2012; 3:1-5]. Aβ is reversibly precipitated by zinc and copper and coordinates these metals in plaques [Adlard et al., Metals and Alzheimer's disease *J Alzheimer's Dis* 2006; 10:145-163; Opazo et al., Metalloenzyme-like activity of Alzheimer's disease β-amyloid: Cu-dependent catalytic conversion of dopamine, cholesterol and biological reducing agents to neurotoxic $H_2O_2$. *J Biol Chem* 2002; 277:40302-40308]. In particular, intracerebral zinc levels are highly abnormal in AD. Postmortem analysis of brain samples in patients with AD showed that cortical zinc levels correlate with cognitive impairment [Religa et al., Elevated cortical zinc in Alzheimer disease. *Neurology* 2006; 67:69-75]. The accumulation of zinc in extracellular Aβ plaque may be acting as either an enhanced source of extracellular zinc or a pathological "zinc sink" resulting in abnormal zinc levels available to the cortical neurons [Craddock et al., The zinc dyshomeostasis hypothesis of Alzheimer's disease. *PLoS One.* 2012; 7(3):e33552. doi:10.1371/journal.pone.0033552]. The high accumulation of zinc in Aβ plaques may lead to a depletion of zinc in the neurons, resulting in abnormal function of zinc-dependent enzymes and structural proteins [Craddock et al., The zinc dyshomeostasis hypothesis of Alzheimer's disease. *PLoS One.* 2012; 7(3):e33552. doi:10.1371/journal.pone.0033552]. Zinc dyshomeostasis may also contribute to abnormal neurotransmission in AD. Zinc is present in the presynaptic vesicles of ~50% of glutamatergic neurons and is co-released into the synapse with glutamate [Watt et al., The role of zinc in Alzheimer's disease. *Int J Alzheimer's Dis.* 2010; 2011:971021]. Zinc causes both voltage-independent and voltage-dependent inhibition of the NMDA receptor [Chen et al., Differential sensitivity of recombinant N-methyl-D-aspartate receptor subtypes to zinc inhibition. *Mol Pharmacol* 1997; 51:1015-1023]. Synaptic zinc has also been suggested to potentiate the toxic effects of Aβ oligomers (Aβ) at NMDAR [Deshpande et al., A role for synaptic zinc in activity dependent Abeta oligomer formation and accumulation at excitatory synapses. *J Neurosci.* 2009 Apr. 1; 29(13):4004-15; Adlard et al., Rapid restoration of cognition in Alzheimer's transgenic mice with 8-hydroxy quinoline analogs is associated with decreased interstitial Abeta. *Neuron.* 2008 Jul. 10; 59(443-55]. The link between zinc abnormalities and AD has motivated researchers to develop zinc chelator therapies for AD in an effort to dissociate zinc from AβOs and plaques. One such molecule, PBT2, has reached to Phase-2 clinical trials with promising results: AD patients treated for a 12-week period showed significantly decreased levels of AβO and p-Tau in the cerebrospinal fluid (CSF), and significant improvement of cognitive test scores at the highest dose level (250 mg daily) of drug [Lannfelt et al., Safety, efficacy, and biomarker findings of PBT2 in targeting Abeta as a modifying therapy for Alzheimer's disease: a phase IIa, double-blind, randomised, placebo controlled trial. *Lancet Neurol.* 2008 September; 7(9):779-86; Faux et al., PBT2 rapidly improves cognition in Alzheimer's Disease: additional phase II analyses. *J Alzheimer's Dis.* 2010; 20(2): 509-16].

Abnormal zinc levels can also be implicated in various cancers. For example, a normal prostate gland accumulates high levels of zinc. Zinc accumulation by prostate epithelial cells is achieved through the activity of zinc uptake transporter proteins. Clinical and experimental evidence establish that malignant prostate, in contrast to normal prostate, is characterized by a decrease in zinc. Evidence suggests that the loss of the zinc transporter function results in the loss of zinc accumulation, which may lead to the production of prostate cancer cells. The loss of zinc transporter function may also be implicated in the production of pancreatic cancer cells and hepatocellular carcinomas, and also possibly in other diseases like obesity and diabetes.

Thus, needed in the art are reliable noninvasive markers as a PET imaging biomarker of Alzheimer's disease or cancer.

SUMMARY OF THE INVENTION

The present invention overcomes the aforementioned drawbacks by providing reliable noninvasive markers, e.g., radiolabeled [$^{63}$Zn]zinc, as a PET imaging biomarker of Alzheimer's disease or cancer.

Specifically, the present invention relates to a method for producing a solution including a positron emitting zinc cation of $^{63}$Zn, a method for detecting or ruling out Alzheimer's disease in a patient, and for detecting zinc distribution in a patient by using such positron emitting zinc cation of $^{63}$Zn.

In one aspect, the invention provides a method for producing a solution including a positron emitting zinc cation. In the method, a solution target including $^{63}$Cu is bombarded with high energy protons to produce a solution including a positron emitting zinc cation. The positron emitting zinc cation may be $^{63}$Zn. The solution target can be produced by dissolving a $^{63}$Cu powder in an acid to form a $^{63}$Cu solution. The $^{63}$Cu solution can be diluted in water to form the solution target. Preferably, the $^{63}$Cu powder comprises at least 99% of $^{63}$Cu. Preferably, the acid is nitric acid. The solution of the positron emitting zinc cation can be purified to remove impurities such as $^{11}$C and $^{13}$N. The zinc cation can be reacted with an anion to produce a positron emitting zinc compound. Preferably, the anion is citrate. The solution including the positron emitting zinc cation can be passed through a column including a sorbent to adsorb the positron emitting zinc cation on the sorbent; and the positron emitting zinc cation can be eluted off the sorbent.

In another aspect, the invention provides a method for detecting or ruling out Alzheimer's disease in a patient. The method includes the steps of administering to a patient a detectable amount of a pharmaceutically acceptable compound including a zinc cation, wherein the zinc cation is a positron emitter, and wherein the zinc cation is targeted to β-amyloid in the patient; and acquiring an image using a medical imaging technique to detect the presence or absence of β-amyloid in the patient. The medical imaging technique can be positron emission tomography. The positron emitting zinc cation can be $^{63}$Zn. The method may also include the step of comparing the image to a reference image to determine if the patient has an increased amount of β-amyloid compared to the reference image. The reference image can be a control image of a control subject having normal cognitive function. The reference image can be a baseline image from a prior scan of the patient's brain.

In another aspect, the invention provides a method for controlling an imaging system to detect or rule out Alzheimer's disease in a patient that has been administered a detectable amount of a pharmaceutically acceptable compound including a zinc cation, wherein the zinc cation is a positron emitter, and wherein the compound is targeted to β-amyloid in the patient. The method includes the steps of acquiring imaging data in the imaging system and reconstructing from the data an image to detect the presence or absence of β-amyloid in the patient. The imaging system can be a positron emission tomography system. The positron emitting zinc cation can be $^{63}$Zn. The method may also include the step of comparing the image to a reference image to determine if the patient has an increased amount of β-amyloid compared to the reference image. The reference image can be a control image of a control subject having normal cognitive function. The reference image can be a baseline image from a prior scan of the patient's brain.

In another aspect, the invention provides a method for detecting or ruling out cancer in a patient. The method includes the steps of administering to a patient a detectable amount of a pharmaceutically acceptable compound including a zinc cation, wherein the zinc cation is a positron emitter, wherein the zinc cation is targeted to tissue in the patient; and acquiring an image using a medical imaging technique to detect zinc distribution in the tissue in the patient. The medical imaging technique can be positron emission tomography. The cancer may be prostate cancer, pancreatic cancer, or liver cancer. The positron emitting zinc cation can be $^{63}$Zn. The method may also include the step of comparing the image to a reference image to determine if the patient has a decreased amount of zinc uptake in the tissue compared to the reference image. The reference image can be a control image of a control subject not having cancer. The reference image can be a baseline image from a prior scan of the patient's tissue.

In another aspect, the invention provides a method for controlling an imaging system to detect or rule out cancer in a patient that has been administered a detectable amount of a pharmaceutically acceptable compound including a zinc cation, wherein the zinc cation is a positron emitter, and wherein the compound is targeted to tissue in the patient. The method includes the steps of acquiring imaging data in the imaging system and reconstructing from the data an image to detect zinc distribution in the tissue in the patient. The imaging system can be a positron emission tomography system. The cancer may be prostate cancer, pancreatic cancer, or liver cancer. The positron emitting zinc cation can be $^{63}$Zn. The method may also include the step of comparing the image to a reference image to determine if the patient has a decreased amount of zinc uptake in the tissue compared to the reference image. The reference image may be a control image of a control subject not having cancer. The reference image may be a baseline image from a prior scan of the patient's tissue.

In another aspect, the invention provides a method for monitoring effects of treatment of cancer in a patient. The method includes the steps of administering to a patient a detectable amount of a pharmaceutically acceptable compound including a zinc cation, wherein the zinc cation is a positron emitter, wherein the zinc cation is targeted to tissue in the patient; and acquiring an image using a medical imaging technique to detect zinc distribution in the tissue in the patient. The medical imaging technique can be positron emission tomography. The cancer may be prostate cancer, pancreatic cancer, or liver cancer. The method may also include the step of comparing the image to a reference image to determine if the patient has an increased amount of zinc uptake in the tissue compared to the reference image, wherein the reference image is a baseline image from a prior scan of the patient's tissue. The positron emitting zinc cation can be $^{63}$Zn.

In another aspect, the invention provides a method for controlling an imaging system monitoring effects of treatment of cancer in a patient that has been administered a detectable amount of a pharmaceutically acceptable compound including a zinc cation, wherein the zinc cation is a positron emitter, and wherein the compound is targeted to tissue in the patient. The method includes the steps of acquiring imaging data in the imaging system and reconstructing from the data an image to detect zinc distribution in the tissue in the patient. The imaging system can be a positron emission tomography system. The cancer may be prostate cancer, pancreatic cancer, or liver cancer. The method may also include the step of comparing the image to a reference image to determine if the patient has an increased amount of zinc uptake in the tissue compared to the reference image, wherein the reference image is a baseline image from a prior scan of the patient's tissue. The positron emitting zinc cation can be $^{63}$Zn.

In another aspect, the invention provides a method for detecting zinc distribution in a patient. The method includes the steps of administering to a patient a detectable amount of a pharmaceutically acceptable compound including a zinc cation, wherein the zinc cation is a positron emitter; and acquiring an image using a medical imaging technique to detect the distribution of zinc in the patient. The medical imaging technique can be positron emission tomography. The positron emitting zinc cation can be $^{63}$Zn. The $^{63}$Zn can be associated with a complex that binds a protein having a zinc transporter function.

In another aspect, the invention provides a method for controlling an imaging system to detect zinc distribution in a patient that has been administered a detectable amount of a pharmaceutically acceptable compound including a zinc cation, wherein the zinc cation is a positron emitter. The method includes the steps of acquiring imaging data in the imaging system and reconstructing from the data an image to detect the zinc distribution in the patient. The imaging system can be a positron emission tomography system. The positron emitting zinc cation can be $^{63}$Zn. The $^{63}$Zn can be associated with a complex that binds a protein having a zinc transporter function.

The foregoing and other aspects and advantages of the invention will appear from the following description. In the description, reference is made to the accompanying drawings which form a part hereof, and in which there is shown by way of illustration example embodiments of the invention. Such embodiments do not necessarily represent the full scope of the invention, however, and reference is made therefore to the claims and description herein for interpreting the scope of the invention.

BRIEF DESCRIPTION OF THE DRAWINGS

FIGS. 1A and 1B show zinc and copper levels in post-mortem brain samples. AC=age-matched normal controls, SZ=schizophrenia, AD=Alzheimer's disease. FIG. 1C shows the relationship of Clinical Dementia rating scale with brain zinc levels. Data were adopted from Religa et al., Elevated cortical zinc in Alzheimer disease. Neurology 2006; 67:69-75.

DETAILED DESCRIPTION OF THE INVENTION

Figure 1:
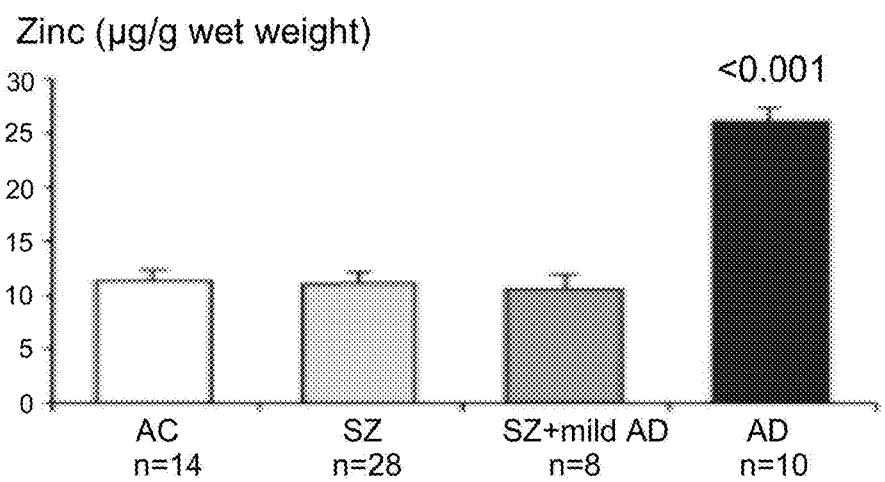
FIG. 1 is a set of graphs showing the relationships between zinc or copper levels and disease conditions in the prior art.
Figure 1:
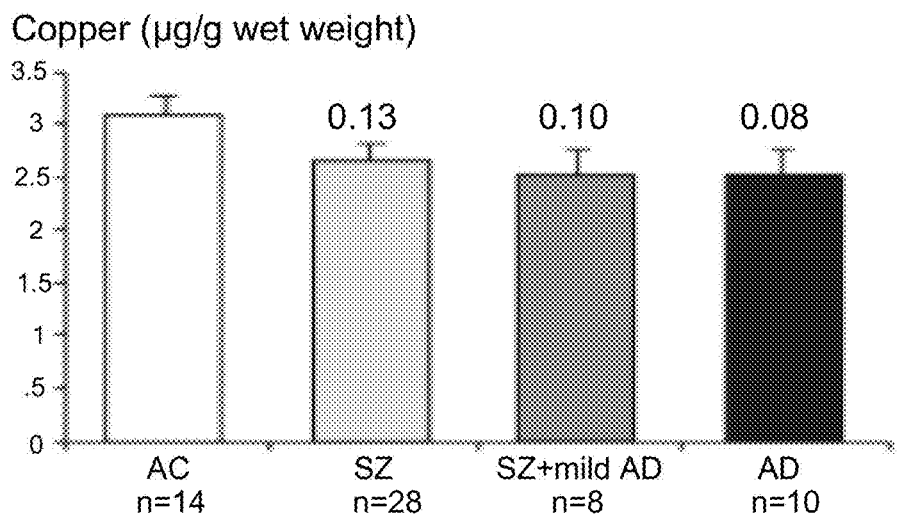
Figure 1:
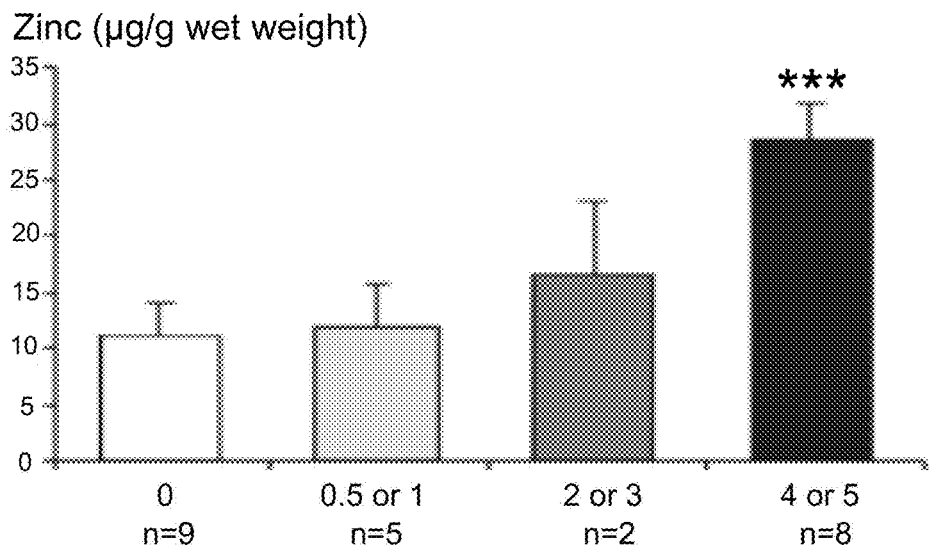

The term "column" or "chromatographic column", as used herein, refers to a separation technique in which the stationary bed is within a tube. The particles of the solid stationary phase or the support coated with a liquid stationary phase, such as resin or sorbent, may fill the whole inside volume of the tube (packed column) or be concentrated on or along the inside tube wall leaving an open, unrestricted path for the mobile phase in the middle part of the tube (open tubular column). Differences in rates of movement through the medium are calculated to different retention times of the sample.

The term "administering" or its other lingual forms as used in the context of the present invention relates to the path by which an agent, a drug, fluid or other substance is brought into contact with the body. The composition is transported from the site of entry to the part of the body where its action is desired to take place. According to one embodiment of the present invention, said administering may be achieved via any medically acceptable means suitable for a composition of the invention or any agent thereof, including rectal, vaginal, nasal, topical, transdermal, or parenteral (including subcutaneous, intramuscular, intrasynovial, intraperitoneal, intradermal and intravenous) administration.

As used herein, the term "patient" refers to a human or non-human mammalian patient suspected of a condition or suffering from a condition in need of treatment.

The present invention is generally applied to humans. In certain embodiments, non-human mammals, such as rats, may also be used for the purpose of demonstration. One may use the present invention for veterinary purpose. For example, one may wish to treat commercially important farm animals, such as cows, horses, pigs, rabbits, goats, and sheep. One may also wish to treat companion animals, such as cats and dogs.

In one aspect, the present invention relates to a method for producing a solution including a positron emitting zinc cation. A positron emitting zinc cation may include any radioactive isotopes of zinc, such as $^{63}$Zn and $^{63}$Zn. In one preferred embodiment, the positron emitting zinc cation of present invention comprises $^{63}$Zn. As a potential PET isotope, $^{63}$Zn possesses a half-life of 38.5 minutes and excellent imaging properties. The half-life may be well-suited for kinetic studies with PET with good signal-to-noise characteristics over a period of 2-3 hours following administration. Previous animal studies showed that zinc is one of the few metal ions that has robust transport across the blood-brain barrier (BBB) ((Kanayama et al., Multitracer screening: Brain delivery of trace elements by eight different administration methods. *BioMetals* 2005; 18:553-565.).

In one embodiment, the present invention may use a high energy proton sources to bombard a target to produce a solution including a positron emitting zinc cation. Any sources for producing high energy protons may be suitable for the present invention. In one specific embodiment, a suitable source for high energy protons may include any particle accelerators, such as cyclotrons, synchrotrons, synchrocyclotrons isochronous cyclotrons and others. In one preferred embodiment, the suitable source for high energy protons may be a cyclotron. High energy protons may have an energy greater than 10 MeV.

In one embodiment, the present method uses a solution target as the starting material to produce a positron emitting zinc cation-containing solution, such as a $^{63}$Zn-containing solution. In one specific embodiment, the solution target may comprise copper cations of $^{63}$Cu. In another specific embodiment, the copper cations of $^{63}$Cu may be produced from a powder of $^{63}$Cu. The powder of $^{63}$Cu may be obtained from any suitable sources. In one embodiment, the powder of $^{63}$Cu may be purchased from a commercial source, for example Cambridge Isotope Laboratory, Massachusetts, USA. Preferably, the powder $^{63}$Cu may be isotopically enriched. For example, a suitable powder of $^{63}$Cu may include at least 90%, preferably at least 95%, more preferably at least 99% of isotopically enriched $^{63}$Cu.

In one embodiment, after a $^{63}$Cu powder is obtained, the $^{63}$Cu powder is converted into a $^{63}$Cu solution. Any suitable method may be used to convert the $^{63}$Cu powder into a $^{63}$Cu solution. Specifically, the $^{63}$Cu powder may be dissolved in an acid to form a $^{63}$Cu solution. In one preferred embodiment, the acid may be any oxidizing acid, such as nitric acid, perchloric acid, chloric acid, chromic acid, and others.

In another embodiment, a suitable acid may include a concentrated sulfuric acid ($H_2SO_4$), a mixture of hydrochloric acid (HCl) and nitric acid ($HNO_3$), usually in a volume ratio of 3:1 (Aqua regia), a mixture of hydrochloric acid (HCl) and hydrogen peroxide ($H_2O_2$), or a mixture of sulfuric acid ($H_2SO_4$) and hydrogen peroxide ($H_2O_2$). In one preferred embodiment, $^{63}$Cu powder may be dissolved in a nitric acid solution to form $^{63}$Cu(NO$_3$)$_2$. In another embodiment, the $^{63}$Cu solution may exist as any other suitable forms such as a hydrate, or as the forms of $^{63}$Cu (NO$_3$)$_2$·xH$_2$O. X may be any suitable number, preferably 1-10, more preferably 1-6.

The nitric acid may have any suitable concentrations. Specifically, the nitric acid may have a concentration greater than 1 M, or greater than 5 M, or greater than 10 M, or greater than 15 M. Preferably, the nitric acid may have a concentration greater than 15 M. In one specific non-limiting example, one may use Stairs' method and equations for the dissolving process [Robert A. Stairs, Copper dissolution in nitric acid, J. Chem. Educ., 1990, 67 (2), p 184].

After the $^{63}$Cu powder dissolves in an acid to form a concentrated $^{63}$Cu solution, the concentrated $^{63}$Cu solution may be diluted into a solution target by adding a solvent. Any suitable solvent may be used for the dilution. Preferably, water may be used to dilute the concentrated $^{63}$Cu solution into a solution target. The present process may also produce any suitable amount of the target solution. A solution target produced from the process may have any suitable concentration. Specifically, a solution target may have a nitric acid concentration especially suitable for subsequent bombardment and irradiation processes. In one preferred embodiment, a solution target may have a concentration in the range of 0.1 M-1 M, preferably 0.2 M-0.8 M, more preferably 0.3 M-0.6 M. For example, a solution target may be prepared by diluting 1 mL of the stock solution (1 mL, 0.42 M) with water (2 mL) to yield a final concentration of 0.14 M $^{63}$Cu in 3 mL. In another embodiment, the concentration of HNO$_3$ in the solution target may be reduced to about a low value, such as 0.1 M, to prevent $^{63}$Cu breakthrough. Applicants note that under a more dilute HNO$_3$ solution, the $^{63}$Cu may get retained at the very top of the column during loading. The $^{63}$Cu nitrate concentration in the target solution may range from 0.1M to 6M.

Figure 4:
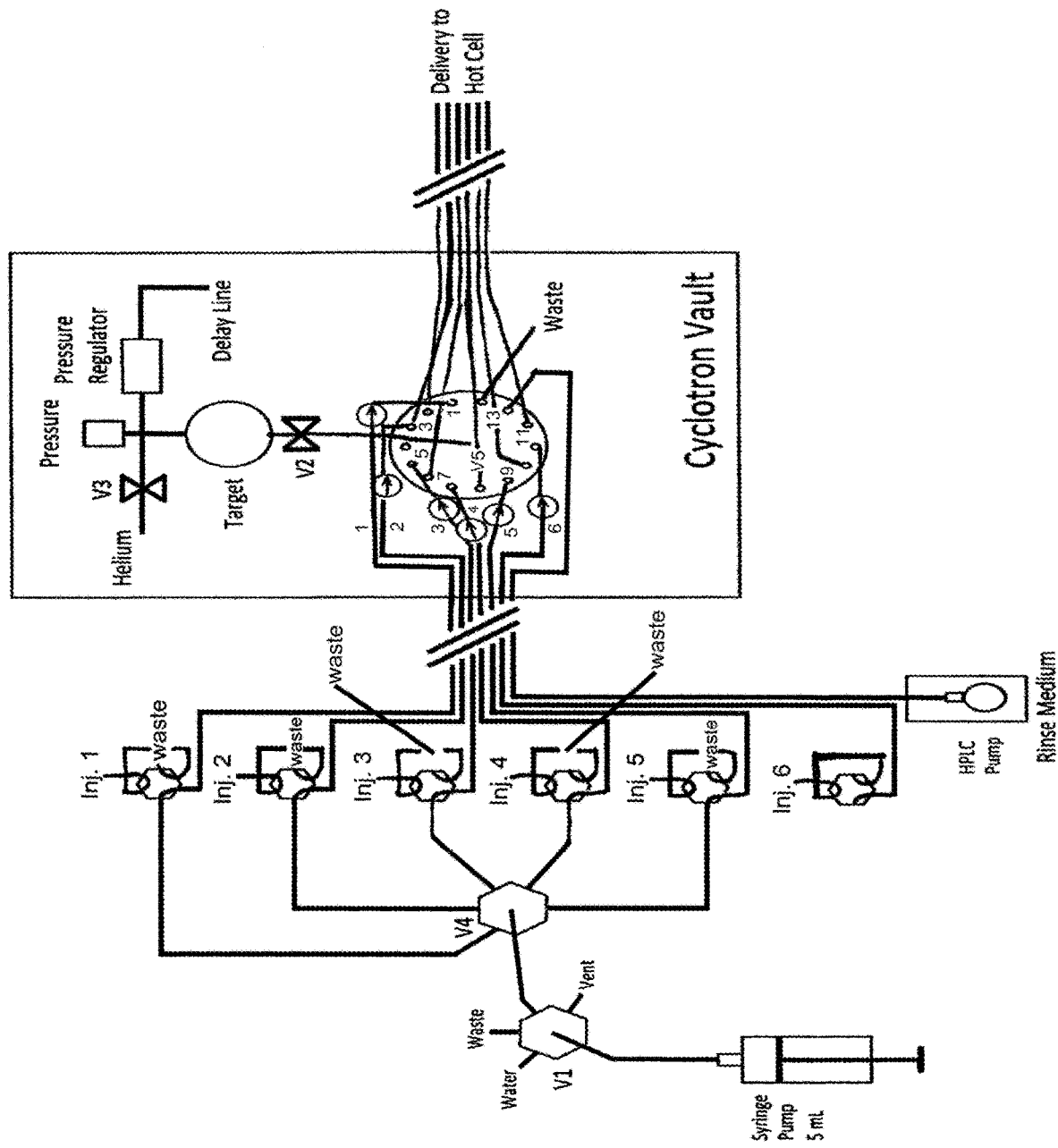
FIG. 4 is a diagram showing a valve system to load a solution target into the cyclotron for a bombarding reaction according to one embodiment of the present invention.

After the production of a solution target, the solution target may be provided to a high energy proton source, preferably a cyclotron, wherein at least some of $^{63}$Cu in the solution target may be converted into $^{63}$Zn following the high energy proton irradiation or bombardment. In one specific embodiment, the solution target may be loaded into a cyclotron by using a valve system. FIG. 4 shows one example of a valve system for loading a solution target into a cyclotron. By using such a system, multiple samples of the solution target may be loaded and subsequently converted into multiple solutions including a positron emitting zinc cation of $^{63}$Zn at the same time.

In one embodiment, a solution target may be pressurized with air or any other suitable gases. Any suitable pressures may be used for pressurizing the solution target. A suitable range of pressure may be 1-100 psi, preferably 20-80 psi, more preferably 30-60 psi. In one specific embodiment, the pressure may be in the range of 40-45 psi.

In one embodiment, a solution target may be irradiated under the power range of 1-1000 μA, preferably 2-500 μA, more preferably 5-200 μA, most preferably 10-100 μA. In one embodiment, a solution target may be irradiated for any suitable amount of time to convert at least some of the $^{63}$Cu in the solution target into $^{63}$Zn. A suitable amount of time may be in the range of 1-1000 minutes, preferably 3-500 minutes, more preferably 5-200 minutes, most preferably 10-100 minutes. In one preferred embodiment, a solution target may be irradiated under cyclotron for 20 to 60 minutes for converting at least some of the $^{63}$Cu in the solution target into $^{63}$Zn.

In one embodiment, during the irradiation or bombarding process, the pressure in the solution target would rise due to the production of gases, such as Hz, O$_2$ and NO$_2$. A valve system such as the one shown in FIG. 4 may be employed to release the pressure. For example, a back pressure valve may be employed to prevent target window rupture. In another embodiment, an evolution of Hz, O$_2$ and NO$_2$ in the solution target during the irradiation process may be monitored by any other suitable indicators. A suitable indicator may include a volume changed in a Hamilton syringe after it is connected to the solution target. In another embodiment, during the irradiation or bombarding process, a conical shape target can provide enhanced heat exchange capacity, resulting in reduced gas formation during irradiation that enables the target to be run as a closed system, pressurized at ~40 psi with oxygen.

After irradiation, a solution comprising at least some $^{63}$Zn is produced. The resulting solution may also include some isotope impurities. Some of the typical isotope impurities may include $^{13}$N and $^{11}$C, which may be formed during the irradiation or bombarding processes. Additionally, the resulting solution may also include a significant amount of $^{63}$Cu, the starting material. In one embodiment, the resulting solution after the irradiation or bombarding processes may be purified to remove at least some of the impurities and the starting material. The resulting solution may be purified by using any suitable processes.

Figure 5:
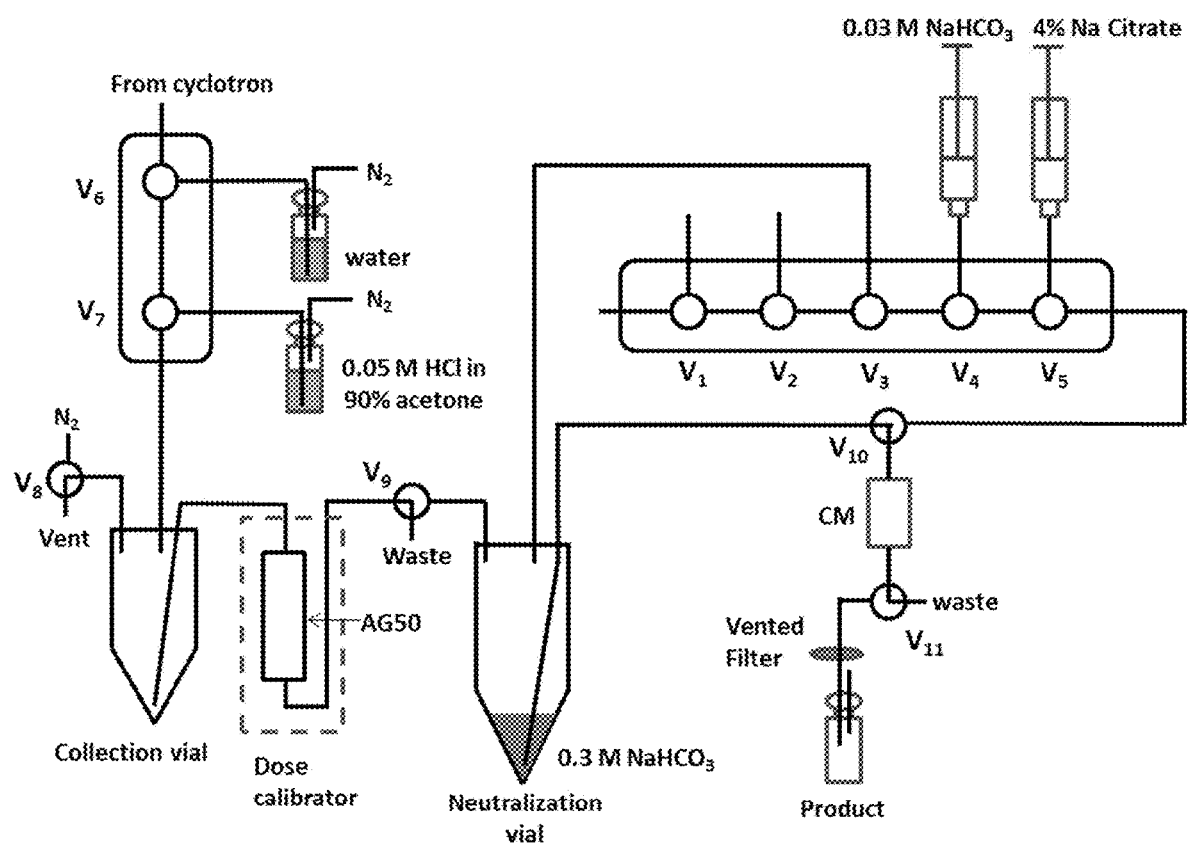
FIG. 5 is a schematic of an automated module for preparation of $^{63}$Zn citrate. Valves V1-V5 are comprised of a disposable cassette that is mounted to the front of the module. All other valves are non-disposable Teflon solenoid valves.

In one specific embodiment, the resulting solution may be purified by using a system shown in FIG. 5 for a remotely operated Cu/$^{63}$Zn separation. For example, as shown in FIG. 5, the resulting solution comprising $^{63}$Zn may be delivered to a vial using the valve system (FIGS. 4 and 5). The target may be rinsed with a solvent such as water and the rinsed solvent may be delivered to the same vial containing the resulting solution of $^{63}$Zn.

In one embodiment, the resulting solution comprising $^{63}$Zn may be purified to remove impurities, such as isotope impurities of $^{13}$N$^3$ and $^{11}$C. Any suitable methods may be used to remove isotope impurities. In one specifically embodiment, a column, specifically a chromatographic column may be used to remove isotope impurities of $^{13}$N, $^{11}$C and others. For example, a commercially available column, such as the Econo-Column® may be used. Any suitable resin or sorbent may be used in the column for removing isotope impurities. A suitable resin or sorbent may include any resins which can trap Cu/$^{63}$Zn but cannot trap isotope impurities such as $^{13}$N and $^{11}$C. In one specific embodiment, the AG®50W-X8 resin may be used.

In one specific example, a slurry in water of the AG®50W-X8 resin may be made and the slurry may be subsequently loaded into the Econo-Column®. The column may be washed with an acid such as HCl. The column may then be flushed with a solvent such as water. The above solution comprising $^{63}$Zn following irradiation may be delivered to a dilution chamber where the solution may be diluted. For example, a solution comprising $^{63}$Zn with a HNO$_3$ concentration of 0.42 M may be diluted into a solution having HNO$_3$ concentration of about 0.2 M.

The diluted solution may be loaded onto to a column, such as the AG®50W-X8 column, at any suitable flow rate. In one specific embodiment, a suitable flow rate may be about 2 mL/min. The column may be washed with a solvent such as H$_2$O to remove any isotope impurities of $^{13}$N and $^{11}$C that formed during the irradiation.

After the removal of the isotope impurities, the Cu/$^{63}$Zn may be eluted with a suitable solvent or a solvent mixture, preferably HCl:acetone, more preferably 0.05 M HCl:90% acetone. In one preferred embodiment, a suitable solvent may elute only $^{63}$Zn but not $^{63}$Cu. As shown in FIG. 5, after the elution, the solution of $^{63}$Zn in the absence of isotope impurities may be neutralized by adding a base, such as NaHCO$_3$.

In another embodiment, the solution of $^{63}$Zn in the absence of isotope impurities may be further purified to remove solvents such as acetone and NaHCO$_3$. After the addition of an excess of aqueous NaHCO$_3$, the $^{63}$Zn within the neutralized solution may be trapped in any suitable filter system for a subsequent wash process. A suitable filter system may include a cartridge. In one specific example, a commercial cartridge, such as a Waters Sep-Pak CM cartridge may be used. For example, the $^{63}$Zn within the neutralized solution may be trapped on a CM cartridge and subsequently the CM cartridge may be washed with a suitable solvent such as water to remove the acetone and to re-dissolve the NaHCO$_3$. In one embodiment, the resulting solution of $^{63}$Zn may be eluted with sodium citrate to form a desired injectable solution.

In one embodiment, $^{63}$Cu(NO$_3$)$_2$·xH$_2$O or $^{63}$Cu(NO$_3$)$_2$ may be recycled. As shown in FIG. 5, the column, such as the AG®50W-X8 column, may be washed from the "bottom" with a solvent such as water and the $^{63}$Cu may be eluted with HNO$_3$. The column may be washed with water from the "top" to remove any residual acid and re-used. The $^{63}$Cu in HNO$_3$ may be dried down on a rotary evaporator and form a solution in 0.4 M HNO$_3$.

Applicants note that an increase in $^{63}$Cu(NO$_3$)$_2$·xH$_2$O or $^{63}$Cu(NO$_3$)$_2$ concentrations, such as from 1.23 M to 1.7 M, may change the production yield, such as from 2.0 to 3.1 GBq, corrected to end of bombardment. Applicants envision that it is possible to increase the $^{63}$Zn yield by increasing the $^{63}$Cu(NO$_3$)$_2$·xH$_2$O concentration even more, increasing the beam current and possibly needing to use a higher acid concentration.

In another aspect, the present invention relates to a method for detecting or ruling out Alzheimer's disease in a patient. In certain embodiments, the present invention provides a method of detecting or ruling out Alzheimer's disease comprising administering a $^{63}$Zn solution as described above to a patient, and imaging the patient by means of a medical imaging technique such as positron emission tomography (PET), wherein the compound is employed as a tracer or biomarker.

In one embodiment, the method for detecting or ruling out Alzheimer's disease in a patient, comprises administering to a patient a detectable amount of a pharmaceutically acceptable compound including a zinc cation, wherein the zinc cation is a positron emitter, wherein the zinc cation is targeted to β-amyloid (Aβ) in the patient.

The present invention generally applies to a mammalian patient such as a human. In some embodiments, the present invention may be also applicable to a non-mammalian patient.

In one embodiment, a suitable amount of a $^{63}$Zn solution of zinc cation may be administered to a patient. The $^{63}$Zn solution of zinc cation may be stabilized in any anion solution, such as citric anion. Depending on the characteristic of a patient, the suitable amount of a $^{63}$Zn solution of zinc cation may be any amount to be detectable under a technique such as a positron emission tomography (PET). The $^{63}$Zn solution of zinc cation may be administered to a patient by using any suitable means. In one preferred embodiment, the $^{63}$Zn solution of zinc cation may be administered to a patient intravenously (IV). In another preferred embodiment, the $^{63}$Zn solution of zinc cation may be administered to a patient by additional methods of intraperitoneal (IP), intramuscular (IM), subcutaneous (SC), intracutaneous (IC), intranasal (IN), peroral (PO), and percutaneous (PC) administration.

In one embodiment, after administering a suitable amount of the $^{63}$Zn solution of zinc cation, the patient may be examined under an imaging technique. In one embodiment, the imaging technique may be a nuclear medical imaging technique that produces a three-dimensional image or picture of functional processes in the body. In one preferred embodiment, the nuclear medical imaging technique may be a positron emission tomography (PET). Generally, a PET system may detect pairs of gamma rays emitted indirectly by a positron-emitting radionuclide (tracer; such as $^{63}$Zn), which is introduced into the body on a biologically active molecule. Three-dimensional images of tracer concentration within the body may be then constructed by computer analysis. In modern scanners, three dimensional imaging may be often accomplished with the aid of a CT X-ray scan performed on the patient during the same session, in the same machine. If the biologically active molecule chosen for PET is FDG, an analogue of glucose, the concentrations of tracer imaged will indicate tissue metabolic activity by virtue of the regional glucose uptake. Use of this tracer to explore the possibility of cancer metastasis (i.e., spreading to other sites) is the most common type of PET scan in standard medical care (90% of current scans). However, on a minority basis, many other radiotracers may be used in PET to image the tissue concentration of many other types of molecules of interest.

In one embodiment, some of the $^{63}$Zn solution of zinc cation may be targeted to β-amyloid in the patient. Using a PET technique, the bio-distribution of radioactivity of $^{63}$Zn may be measured in the body of the patient.

In another embodiment, the method for detecting or ruling out Alzheimer's disease in a patient further comprises acquiring an image using positron emission tomography to detect the presence or absence of β-amyloid (Aβ) in the patient.

Figure 3:
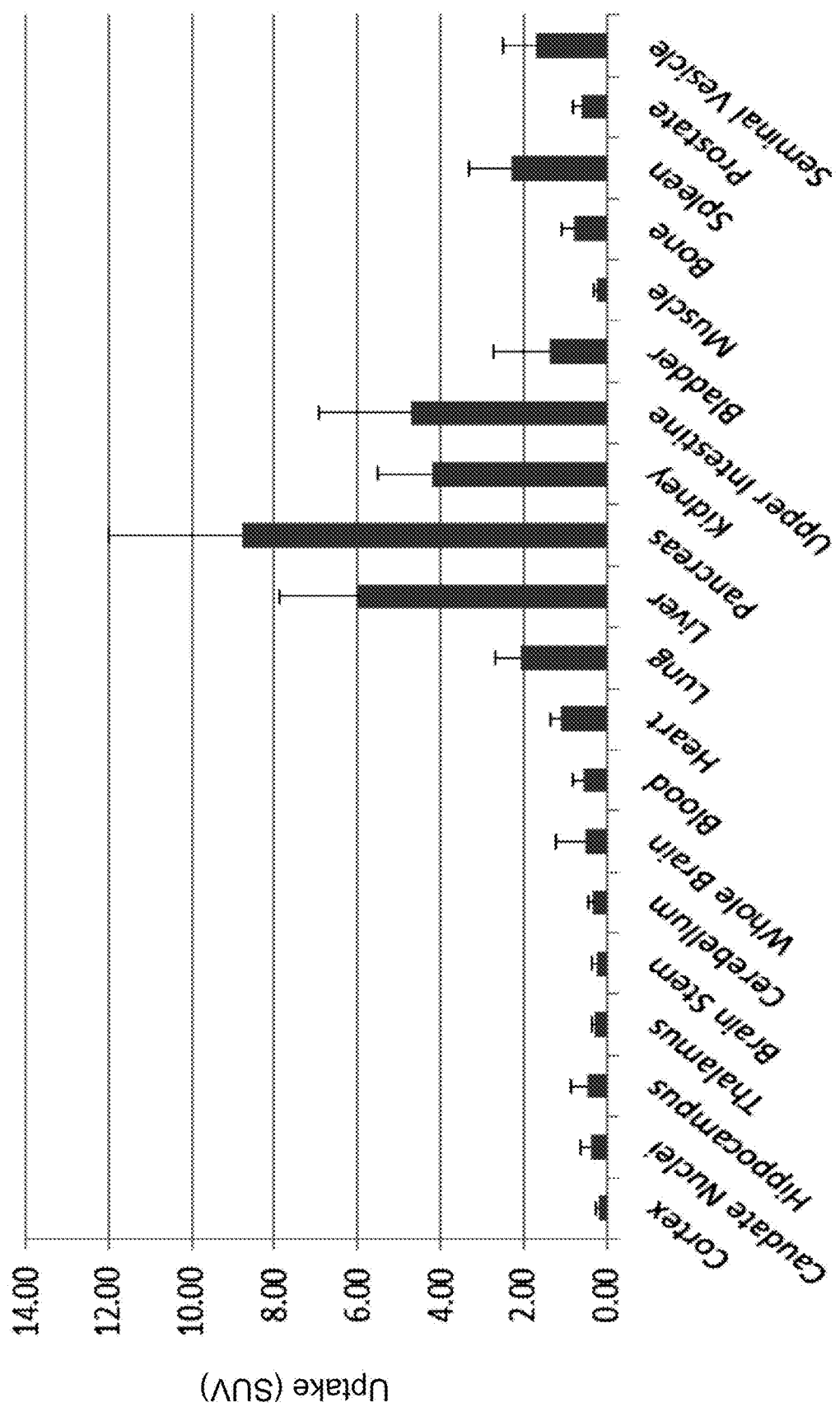
FIG. 3 is a graph showing biodistribution of $^{63}$Zn citrate in normal mice at 1 hour after IV according to one embodiment of the present invention.

FIG. 3 shows the biodistribution of Zn citrate in normal mice at 1 hour after IV administration. The observations show that $^{63}$Zn is brain penetrant after administering the radiotracer of $^{63}$Zn to five normal male mice intravenously and measured the biodistribution of radioactivity at 1 hour. Uptake may be measured in units of Standardized Uptake Value (SUV)=(uptake/g tissue)/(injected dose/g body mass).

As shown in FIG. 3 and Table 1, high uptake of $^{63}$Zn was found in the pancreas, liver, kidneys, upper intestines, prostate and seminal vesicles. Uptake in brain regions was significant (regional SUVs=0.2-0.5), showing penetration of $^{63}$Zn into the brain. Given that the blood volume in the brain is typically ~5%, the uptake in brain cannot be accounted for by radioactivity in the blood alone.

Figure 2:
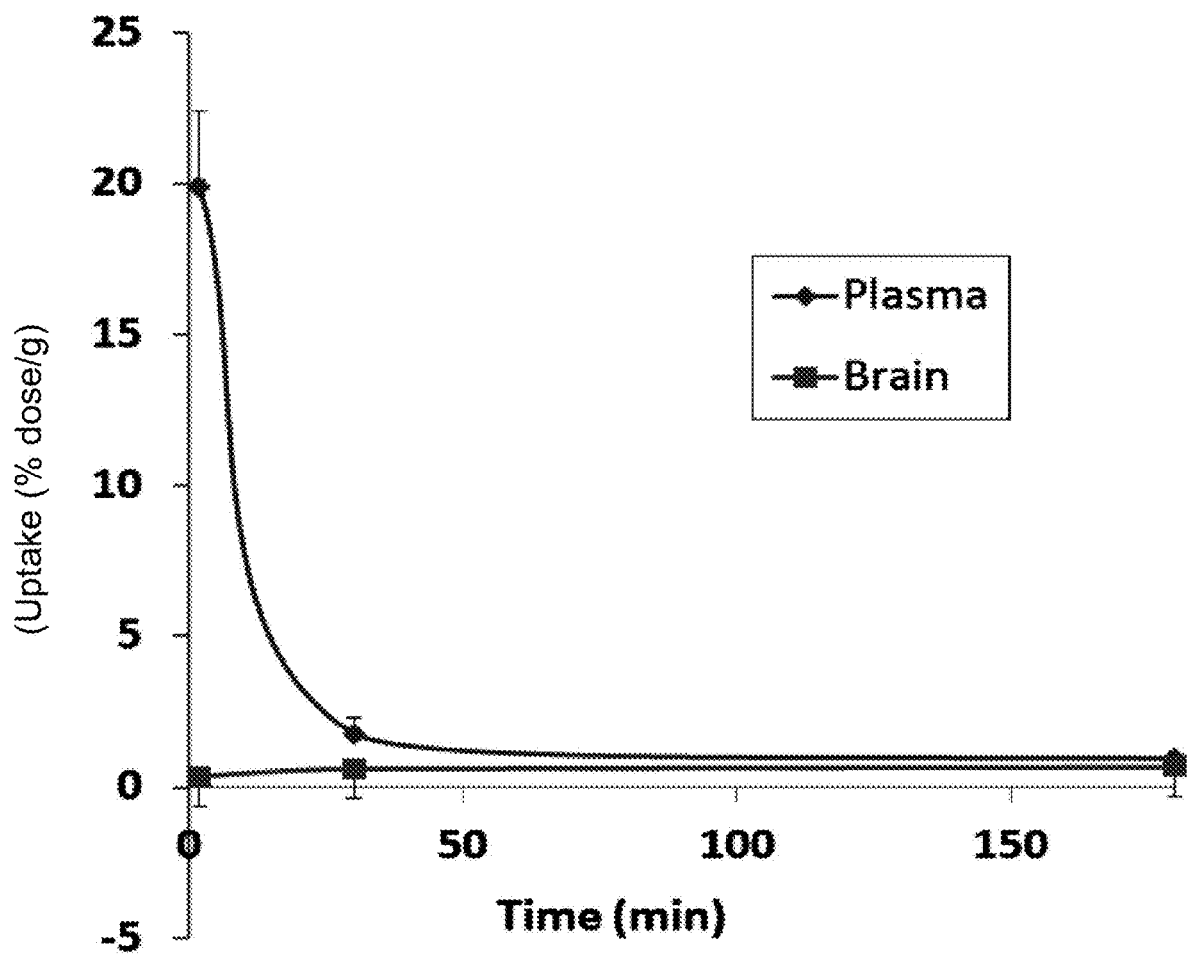
FIG. 2 is a graph showing the kinetics of $^{63}$Zn in mouse plasma and brain after intravenous (IV) injection in the prior art. Data were adopted from Kanayama et al., Multitracer screening: Brain delivery of trace elements by eight different administration methods. *BioMetals* 2005; 18:553-565.

These results were also consistent with a previous study showing uptake of another isotope of zinc, $^{65}$Zn, into mouse brain (FIG. 2). In that study, the longer lived $^{65}$Zn (244 d) allowed determination of transport kinetics to 24 hours. It was seen that brain uptake of zinc has an initial rapid phase in the first hour followed by a slower rise thereafter. Likewise, in the present invention, the majority of plasma clearance may be completed by 1 hour as $^{63}$Zn has a half-life of 38.5 minutes, this will allow imaging with good signal-to-noise characteristics to 2-3 hours. This period of time should be sufficient to determine regional rate constant estimates for blood-to-brain transport (K1) and brain-to-blood transport (k2). Further rate constants that may define intracerebral compartments of zinc that may bind and release zinc (k3, k4, etc.) may be also accessible. It should be noted that in the study of Kanayama et al., zinc uptake in brain at 30 minutes was several fold higher than any of the other metal ions measured (Be, Sc, V, Cr, Mn, Fe, Co, As, Se, Rb, Sr, Y, Zr, Tc, and Ru) demonstrating the robust transport of zinc across the BBB.

TABLE 1

Standardized Uptake Value (SUV) data for $^{63}$Zn Citrate biodistribution in normal mice.

| | SUV data | | | | | | |
|---|---|---|---|---|---|---|---|
| Sample | 1 Wild | 2 Wild | 3 Wild | 4 Wild | 5 Wild | Average | Stand. Dev. |
| Cortex | 0.2 | 0.19 | 0.27 | 0.2 | 0.09 | 0.19 | 0.07 |
| Caudate Nuclei | 0.34 | 0.23 | 0.57 | 0.63 | 0.09 | 0.37 | 0.23 |
| Hippocampus | 0.28 | 0.24 | 0.88 | 0.87 | 0.12 | 0.48 | 0.37 |
| Thalamus | 0.29 | 0.25 | 0.38 | 0.28 | 0.11 | 0.26 | 0.1 |
| Brain Stem | 0.25 | 0.25 | 0.34 | 0.32 | 0.11 | 0.25 | 0.09 |
| Cerebellum | 0.27 | 0.27 | 0.38 | 0.49 | 0.13 | 0.31 | 0.14 |
| Whole Brain | 0.25 | 0.23 | 0.35 | 0.3 | 0.1 | 0.24 | 0.09 |
| Blood | 0.47 | 0.36 | 0.94 | 0.69 | 0.38 | 0.57 | 0.25 |
| Heart | 1.11 | 1.11 | 1.47 | 1.1 | 0.82 | 1.12 | 0.23 |
| Lung | 2.67 | 1.8 | 2.54 | 2.19 | 1.13 | 2.06 | 0.62 |
| Liver | 6.18 | 5.27 | 8.72 | 6.29 | 3.4 | 5.97 | 1.92 |
| Pancreas | 10.67 | 5.25 | 11.95 | 10.68 | 5.33 | 8.78 | 3.22 |
| Kidney | 3.8 | 4.32 | 6.01 | 4.49 | 2.42 | 4.21 | 1.3 |
| Upper Intestine | 3.02 | 2.99 | 7.66 | 6.46 | 3.47 | 4.72 | 2.18 |
| Bladder | 1.27 | 3.66 | 1.13 | 0.73 | 0.18 | 1.39 | 1.33 |
| Muscle | 0.2 | 0.19 | 0.31 | 0.26 | 0.1 | 0.21 | 0.08 |
| Bone | 0.72 | 0.5 | 1.11 | 1.11 | 0.38 | 0.76 | 0.34 |
| Spleen | 2.37 | 1.8 | 3.71 | 2.62 | 0.97 | 2.3 | 1.01 |
| Prostate | ~ | ~ | 0.47 | 0.85 | 0.44 | 0.58 | 0.23 |
| Seminal Vesicle | ~ | ~ | 1.397192 | 2.587523 | 1.09 | 1.69 | 0.79 |

Figure 13:
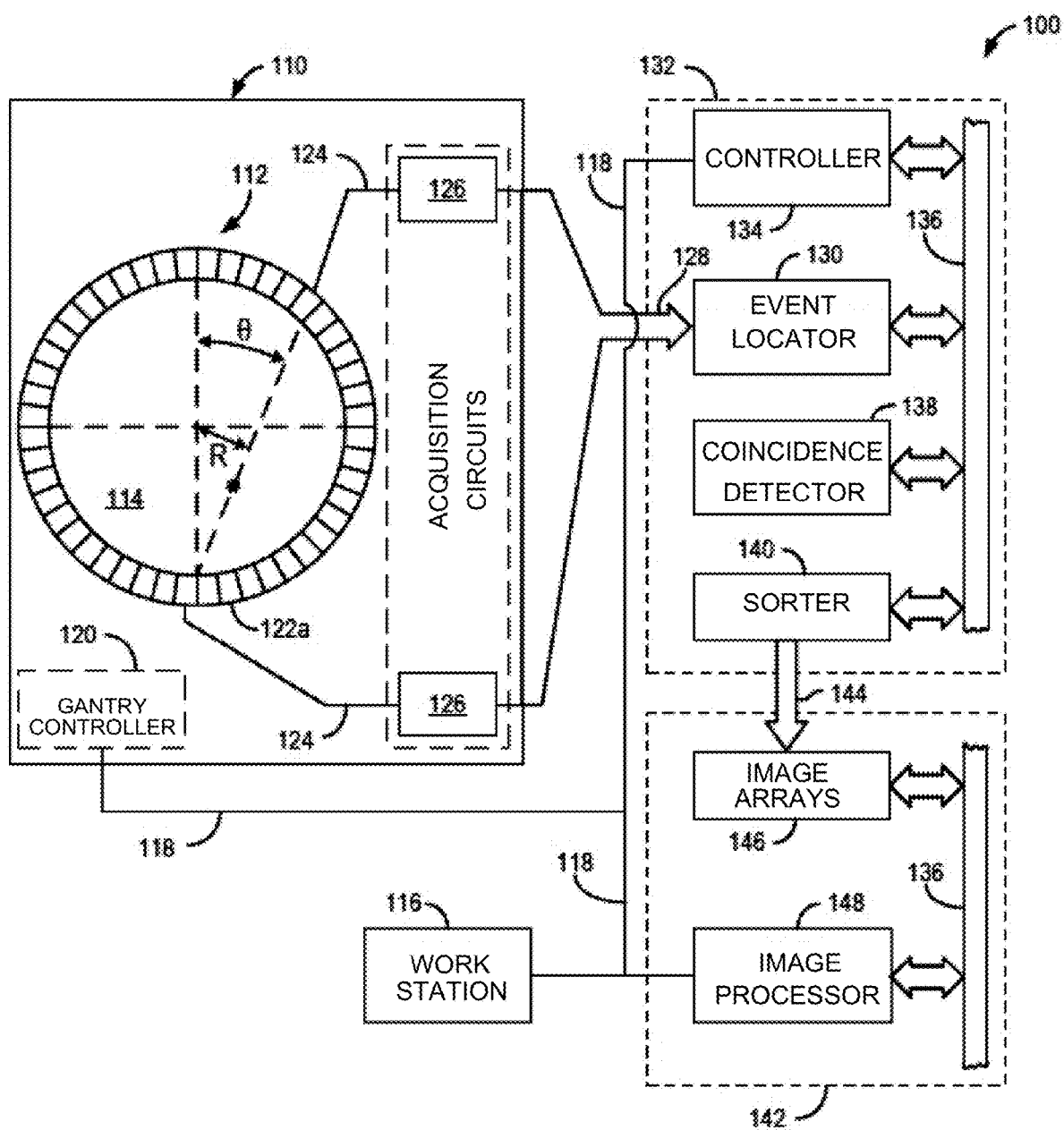
FIG. 13 is a schematic view of an emission tomography system suitable for use in accordance with the present invention.

Referring to FIG. 13, a PET system 100 that can be used in the method of present invention includes an imaging hardware system 110 that includes a detector ring assembly 112 about a central axis, or bore 114. An operator work station 116 including a commercially-available processor running a commercially-available operating system communicates through a communications link 118 with a gantry controller 120 to control operation of the imaging hardware system 110.

The detector ring assembly 112 is formed of a multitude of radiation detector units 122 that produce a signal responsive to detection of a photon on communications line 124 when an event occurs. A set of acquisition circuits 126 receive the signals and produce signals indicating the event coordinates (x, y) and the total energy associated with the photons that caused the event. These signals are sent through a cable 128 to an event locator circuit 130. Each acquisition circuit 126 also produces an event detection pulse that indicates the exact moment the interaction took place. Other systems utilize sophisticated digital electronics that can also obtain this information regarding the precise instant in which the event occurred from the same signals used to obtain energy and event coordinates.

The event locator circuits 130 in some implementations, form part of a data acquisition processing system 132 that periodically samples the signals produced by the acquisition circuits 126. The data acquisition processing system 132 includes a general controller 134 that controls communications on a backplane bus 136 and on the general communications network 118. The event locator circuits 130 assemble the information regarding each valid event into a set of numbers that indicate precisely when the event took place and the position in which the event was detected. This event data packet is conveyed to a coincidence detector 138 that is also part of the data acquisition processing system 132.

The coincidence detector 138 accepts the event data packets from the event locator circuit 130 and determines if any two of them are in coincidence. Coincidence is determined by a number of factors. First, the time markers in each event data packet must be within a predetermined time window, for example, 0.5 nanoseconds or even down to picoseconds. Second, the locations indicated by the two event data packets must lie on a straight line that passes through the field of view in the scanner bore 114. Events that cannot be paired are discarded from consideration by the coincidence detector 138, but coincident event pairs are located and recorded as a coincidence data packet. These coincidence data packets are provided to a sorter 140. The function of the sorter in many traditional PET imaging systems is to receive the coincidence data packets and generate memory addresses from the coincidence data packets for the efficient storage of the coincidence data. In that context, the set of all projection rays that point in the same direction ($\theta$) and pass through the scanner's field of view (FOV) is a complete projection, or "view". The distance (R) between a particular projection ray and the center of the FOV locates that projection ray within the FOV. The sorter 140 counts all of the events that occur on a given projection ray (R, $\theta$) during the scan by sorting out the coincidence data packets that indicate an event at the two detectors lying on this projection ray. The coincidence counts are organized, for example, as a set of two-dimensional arrays, one for each axial image plane, and each having as one of its dimensions the projection angle $\theta$ and the other dimension the distance R. This $\theta$ by R map of the measured events is call a histogram or, more commonly, a sinogram array. It is these sinograms that are processed to reconstruct images that indicate the number of events that took place at each image pixel location during the scan. The sorter 140 counts all events occurring along each projection ray (R, $\theta$) and organizes them into an image data array.

The sorter 140 provides image datasets to an image processing/reconstruction system 142, for example, by way of a communications link 144 to be stored in an image array 146. The image arrays 146 hold the respective datasets for access by an image processor 148 that reconstructs images. The image processing/reconstruction system 142 may communicate with and/or be integrated with the work station 116 or other remote work stations.

The PET system 100 provides an example emission tomography system for acquiring a series of medical images of a patient during an imaging process after administering a pharmaceutically acceptable compound including a $^{63}$Zn cation as described herein. The system includes a plurality of detectors configured to be arranged about the patient to acquire gamma rays emitted from the patient over a time period relative to an administration of the compound including a $^{63}$Zn cation to the patient and communicate signals corresponding to acquired gamma rays. The system also includes a reconstruction system configured to receive the signals and reconstruct therefrom a series of medical images of the patient. In one version of the system, a second series of medical images is concurrently acquired using an x-ray computed tomography imaging device.

EXAMPLES

The following Examples are provided in order to demonstrate and further illustrate certain embodiments and aspects of the present invention and are not to be construed as limiting the scope of the invention.

Example 1

Summary of Example 1

Abnormalities of zinc homeostasis are indicated in many human diseases. A noninvasive imaging method for monitoring zinc in the body would be useful to understand zinc dynamics in health and disease. To provide a PET imaging agent for zinc, we have investigated production of $^{63}$Zn ($T_{1/2}$=38.5 minutes) via the $^{63}$Cu(p,n)$^{63}$Zn reaction using isotopically enriched solutions of [$^{63}$Cu]copper nitrate. A solution target was used for rapid isolation of the $^{63}$Zn radioisotope from the parent $^{63}$Cu ions. Initial biological evaluation was performed by biodistribution in normal mice.

Methods: To produce $^{63}$Zn, solutions of [$^{63}$Cu]copper nitrate (1.23-1.7 M) in 0.1 N HNO$_3$ were irradiated by 14 MeV protons at 20 µA for 60 minutes in a low energy cyclotron. An automated module was used to purify $^{63}$Zn from $^{63}$Cu in the target solution. The $^{63}$Cu/$^{63}$Zn mixture was trapped on a cation-exchange resin (AG 50W-X8, H$^+$ form). The resin was rinsed with water, followed by elution of the $^{63}$Zn using 0.05 N HCl in 90% acetone. The resulting solution was neutralized with NaHCO$_3$, trapped on a carboxymethyl (CM) cartridge, washed with water and eluted with isotonic 4% sodium citrate. Standard quality control tests were performed on the product according to current good manufacturing practice (cGMP), including radionuclidic identity and purity, and quantities of nonradioactive Zn$^{+2}$, Cu$^{+2}$, Fe$^{+3}$, and Ni$^{+2}$ by ion-chromatography. Biodistribution studies were performed in normal mice after intravenous administration of $^{63}$Zn citrate. $^{63}$Cu target material was recycled by eluting the initial resin with 4 N HNO$_3$.

Results: Yields of 933±222 MBq (uncorrected) of $^{63}$Zn citrate were obtained with a 1.23 M [$^{63}$Cu]copper nitrate solution. Radionuclidic purity was >99.9% with copper content <3 µg/batch. Specific activities of 34.2±13.8 MBq/µg (uncorrected) for the $^{63}$Zn product were obtained. Biodistribution in normal mice at 60 minutes showed expected high uptakes in pancreas (SUV=8.8±3.2), liver (6.0±1.9), upper intestine (4.7±2.1) and kidney (4.2±1.3).

Conclusion: A practical and cGMP-compliant preparation of radionuclidically pure $^{63}$Zn citrate has been developed that will enable PET imaging studies in animal and human studies. $^{63}$Zn citrate showed the expected biodistribution in mice.

Introduction to Example 1

Zinc is an essential mineral in the body that is at the reactive center of more than 300 metabolic enzymes and has fundamental roles in protein structure and protein-protein interactions (1). It participates in tertiary, quaternary, and quinary structure of proteins, in protein aggregation, and in the structure of protein domains for interactions with other proteins, DNA/RNA, and lipids. Zinc deficiency affects about two billion people in the developing world (2), while excess zinc consumption can also cause detrimental effects of ataxia, lethargy and copper deficiency. Disruption of zinc homeostasis may be involved in metabolic syndrome, diabetes and diabetic complications (3). Zinc homeostasis may play an important role in certain cancer types, including pancreatic cancer (4), prostate cancer (5), and breast cancer (6). Also, zinc is associated with the aggregation of β-amyloid proteins that accumulate in brains of patients with Alzheimer's Disease (AD) (7). Metal chelation therapy is under investigation for treatment of AD with the intent of altering zinc and copper binding within β-amyloid deposits in the brain (8). Clearly, a noninvasive method to measure zinc dynamics in the body would be of high interest for understanding the pathophysiology of a broad range of diseases. It may also be useful for monitoring therapies that are directed at changing zinc homeostasis.

There are 3 positron-emitting isotopes of zinc that have potential to be used as PET biomarkers of zinc kinetics in living systems: 26 zn, $^{63}$Zn, and $^{65}$Zn (see Table 3). $^{62}$Zn ($T_{1/2}$=9.26 h) is compromised for imaging of zinc biodistribution because its daughter isotope $^{62}$Cu is also a positron emitter that may confound the interpretation of the PET images. Nevertheless, $^{62}$Zn has been effectively used preclinically as a zinc biomarker of pancreatic exocrine function (9). $^{65}$Zn is impractical for clinical imaging due to its 244 day half-life, but has served as a zinc biomarker in central nervous system investigations (10). The potential of $^{63}$Zn as a PET imaging tracer is supported by its attractive physical decay characteristics ($T_{1/2}$=38.5 m, mean $\beta^+$ energy=0.99 MeV, total $\beta^+$ intensity=93%), and the feasibility of cyclotron production via the $^{63}$Cu(p,n)$^{63}$Zn reaction in low energy proton accelerators (11, 12). Although the shorter half-life of $^{63}$Zn may limit its ability to assess longer biological turnover times, it is sufficient to monitor initial transport of zinc from the blood to tissues, and further transport processes that have turnover times on the order of 2 hours or less. For example, $^{63}$Zn should be well suited to study transport kinetics of zinc into pancreas, prostate or across the blood-brain barrier.

$^{63}$Zn has been produced by irradiating natural copper foils with protons through the natCu(p,n)$^{63}$Zn nuclear reaction that exhibits high cross section values at low proton energies (11, 12). Since natural copper is composed of 69.2% $^{63}$Cu and 31.8% $^{65}$Cu, small fractions of $^{65}$Zn was produced via the $^{65}$Cu(p,n)$^{65}$Zn reaction which would preclude applications in clinical imaging. In the present study of Example 1, we investigate the feasibility to produce pure $^{63}$Zn by utilizing isotopically enriched $^{63}$Cu as parent material. Based on our recent findings on solution targets (13), we now report use of a solution target filled with [$^{63}$Cu]copper nitrate in dilute nitric acid to produce $^{63}$Zn. A methodology for rapid separation of the $^{63}$Zn product from $^{63}$Cu was also developed. Although lower quantities of $^{63}$Zn can be produced in a solution target relative to a solid target, isotopically enriched $^{63}$Cu foils are not commercially available, and the solution target approach avoids the need to dissolve the target after irradiation, thus saving time in the purification process. The purification process was automated using a radiochemistry module. Finally, the $^{63}$Zn citrate product was preliminarily evaluated for uptake characteristics by biodistribution in normal mice.

Materials and Methods for Example 1

Materials

The AG®50W-X8 (H$^+$ form) resin (Bio-Rad, Hercules, Calif., USA) was used as received and slurry packed with water into glass Econo-Column® (Bio-Rad, Hercules, Calif., USA). The water (18 mΩ) was generated in-house (Barnstead Nanopure system by Thermo Scientific). The HCl and HNO$_3$ were obtained as Trace Metal Grade from Fisher Scientific (Pittsburgh, Pa., USA). Isotopically enriched $^{63}$Cu metal (99.9% enrichment) was obtained from Cambridge Isotope Laboratories (Cambridge, Mass., USA). Acetone and NaHCO$_3$ were obtained from Sigma-Aldrich (St. Louis, Mo., USA). Sterile 4% sodium citrate solution, USP, was obtained from Fenwal Inc, (Lake Zurich, Ill., USA). Sep-Pak CM Light cartridges (Waters Corp., Milford, Mass., USA) were pre-rinsed with 5 mL water. The activity readings were recorded using a CRC dose calibrator (#480 setting, CRC-55tPET).

Target And Target Solution

A PETtrace cyclotron (GE Healthcare, Milwaukee, Wis., USA) was used. The solution target was developed in-house as previously described (14). Briefly, it consisted of a 1.6 mL water-cooled tantalum target insert that was separated from the cyclotron by dual foils (Al and Havar) with a helium cooling channel in between. Incident proton energy was degraded from 16.4 MeV to ~14 MeV at the target solution. The isotopically enriched $^{63}$Cu powder (99.9% enriched, 1.0 g, 15.9 mmol) was dissolved in excess HNO$_3$ and then evaporated to dryness under vacuum to form $^{63}$Cu(NO$_3$)$_2$·xH$_2$O. By weighing the dried material (3.8 g), we estimated that the ratio of water molecules to copper nitrate was approximately 3. To prepare a 1.7 M $^{63}$Cu(NO$_3$)$_2$ target solution, 0.74 g $^{63}$Cu(NO$_3$)$_2$·xH$_2$O and 12 mL concentrated nitric acid were added to sufficient water to bring the total volume to 1.8 mL. The concentration of HNO$_3$ (~0.1 N) was sufficient to prevent in-target precipitation of copper hydroxide while reducing water radiolysis (13).

Production and Purification of $^{63}$Zn

The Cu(NO$_3$)$_2$·xH$_2$O solution (1.8 mL) was loaded into the cyclotron target using an automated valve system (13, 14). The target was pressurized with air (40-45 psi) and irradiated at 20 μA for 60 minutes. Pressure rose in the target until reaching a plateau of 110-130 psi at ~20 minutes after start of irradiation. After irradiation, the target material was delivered to an in-house developed automated radiosynthesis module (see FIG. 5) for further processing. The target material was first delivered into a collection vial in the hot cell. The target was rinsed with water (1.8 mL) that was delivered to the same collection vial to yield a final volume of ~3.6 mL. Both $^{63}$Zn and $^{63}$Cu were trapped on a column of AG®50W-X8 resin (6 g) which was prewashed with 4 N HNO$_3$ (5 mL) and then flushed with water (75 mL) before each production and placed in a dose calibrator for measurement of trapped radioactivity. The $^{63}$Zn solution was loaded onto to the AG®50W-X8 column at a flow rate of ~2 mL/min. The column was washed with 9 mL water to remove $^{13}$N and $^{11}$C byproducts that were formed during the irradiation. Following the work of Guerra-Gomez (12), the $^{63}$Zn was eluted with 0.05 M HCl in 90% acetone (30 mL) and transferred to a 100 mL "neutralization flask" that was prefilled with 8 mL of a 0.3 M NaHCO$_3$ solution. After brief stirring, the resulting mixture was passed through a CM cartridge (Waters CM Sep-Pak Light) under 20 psi driving pressure. The CM cartridge was washed with 0.03 M NaHCO$_3$ (10 mL) to remove the acetone without loss of $^{63}$Zn. Finally, the product was eluted from the CM cartridge with 2-5 mL 4% sodium citrate USP solution, passed through a 0.2 m sterilizing filter, and collected in a sterile empty vial. In initial runs, metal needles were avoided, but in final runs performed according to Current Good Manufacturing Practice (cGMP), disposable metal needles were used in the process of sterile filtration, procurement of the quality control sample, and dilution of the product (2 mL) was performed with sterile saline (8 mL).

Recycling of $^{63}$Cu

The $^{63}$Cu(NO$_3$)$_2$ was recycled by washing the AG®50W-X8 column in retrograde direction with water (20 mL), followed by elution (again retrograde) of the $^{63}$Cu with 4 N HNO$_3$ (~20 mL). The column was further washed with water (75 mL) to remove any residual acid. In initial runs, the AG column was reused. For the final runs that were performed according to cGMP, the AG column was prepared fresh before each run. The recovered $^{63}Cu(NO_3)_2$ solution was dried under vacuum and the residual $^{63}Cu(NO_3)_2$ $xH_2O$ reconstituted in 0.1 M $HNO_3$ as described above.

Quality Control of $^{63}Zn$ Citrate Product

The $^{63}Zn$ citrate product was submitted for standard quality control analyses for radiopharmaceutical preparation, including optical clarity by appearance, pH, radionuclidic identity (half-life), radionuclidic purity (High purity Germanium gamma spectroscopy, Canberra DSA-1000, Meridan, Conn., USA), residual solvents (GC-FID, SRI Instruments, Torrence, Calif., USA), filter integrity, pyrogens (endotoxin test) and sterility. For radiochemical identity, radiochemical purity, and chemical purity, the QC samples were analyzed using an HPLC (Dionex, ICS-5000, ThermoFisher, Pittsburgh Pa., USA), equipped with an IonPac CSSA analytical column (4×250 mm, Dionex) and PC10 post-column pneumatic delivery system (Dionex) to mix the dye 4-(2-pyridylazo)resorcinol (PAR) (Dionex) for spectrophotometric detection at 530 nm of $Zn^{+2}$, $Cu^{+2}$, $Fe^{+3}$, and $Ni^{+2}$. The flow rate of mobile phase (Dionex MetPac Eluent) was 1.2 mL/min. The flow rate of PAR diluent was 0.6 mL/min. The HPLC also had in-line radioactivity detection (Carroll and Ramsey, Berkeley, Calif., USA). Because the radioactivity detector was placed before the post-column PAR dilution manifold, there was a ~0.3 minute delay between the radioactivity and UV data.

Biodistribution of $^{63}Zn$ Citrate in Mice

Biodistribution characteristics of $^{63}Zn$ citrate were investigated in male B6.SJL mice (n=4) (Jackson Laboratories, Bar Harbor, Me., USA) under the approval of the Mayo Clinic Institutional Animal Care and Use Committee. Animals were administered $^{63}Zn$ citrate (~1.8-3.6 MBq) into a tail vein and euthanized at 60 minutes for biodistribution analysis. Tissues were weighed and counted for radioactivity. Biodistribution data were expressed as Standard Uptake Value (SUV)=(counts/g)tissue/(injected dose counts/wt. of mouse (g)).

Statistics

Biodistribution data was expressed as mean±sd. Statistical comparison of analytical data between groups of runs was performed using the two-tailed Student's T-test. Statistical comparison of intracerebral regional uptake of $^{63}Zn$ was performed using ANOVA. P-values <0.05 were considered statistically significant.

Results for Example 1

Production and Isolation of $^{63}Zn$

Proton irradiations of $^{63}Cu(NO_3)_2$ solutions (1.7 M or 1.23 M) were performed for 60 minutes at 20 μA (Table 4). After the target rinse dilution to ~0.05 M $HNO_3$, both the $^{63}Cu$ and $^{63}Zn$ were trapped on the AG®50W-X8 cation-exchange resin (see AG50 in FIG. 5). A further 9 mL water rinse removed a large fraction of the $^{13}N$, $^{11}C$, and $^{18}F$ contaminants generated during the irradiation. $^{63}Zn$ was eluted from the AG column by washing with 30 mL 0.05 M HCl in 90% acetone. The elution of $^{63}Zn$ from the AG column was followed by monitoring the amount of radioactivity in the dose calibrator. The $^{63}Zn$ was then collected in a vial and neutralized with pre-addition of 8 mL 0.3 N $NaHCO_3$. This mixture was then passed through a Sep-Pak CM Light cartridge, effectively trapping the $^{63}Zn$. After rinsing the CM cartridge with 10 mL of a 0.03 M $NaHCO_3$ solution, the product was eluted from the CM cartridge with 2-5 mL 4% sodium citrate USP solution, passed through a 0.2 m sterilizing filter, and collected in a sterile empty vial. The time of processing was 36±3 minutes. Saturated yields of processed $^{63}Zn$ citrate were 309±17 MBq/μA and 160±17 MBq/μA, respectively, for 1.7 M and 1.23 M $^{63}Cu(NO_3)_2$ solutions (Table 4). An uncorrected yield of 1.53±0.10 GBq of $^{63}Zn$ citrate was obtained from 60 minute irradiations of 1.7N $^{63}Cu(NO_3)_2$ solution (n=3). This yield was similar to the ~1.4 GBq yield reported by Guerra-Gómez by irradiation and processing of solid natural copper foil (12). $^{63}Cu(NO_3)_2$ was successfully recovered (>85% recovery) and re-irradiated several times with no degradation of radionuclidic purity of $^{63}Zn$ product.

Quality Control Tests

Figure 6:
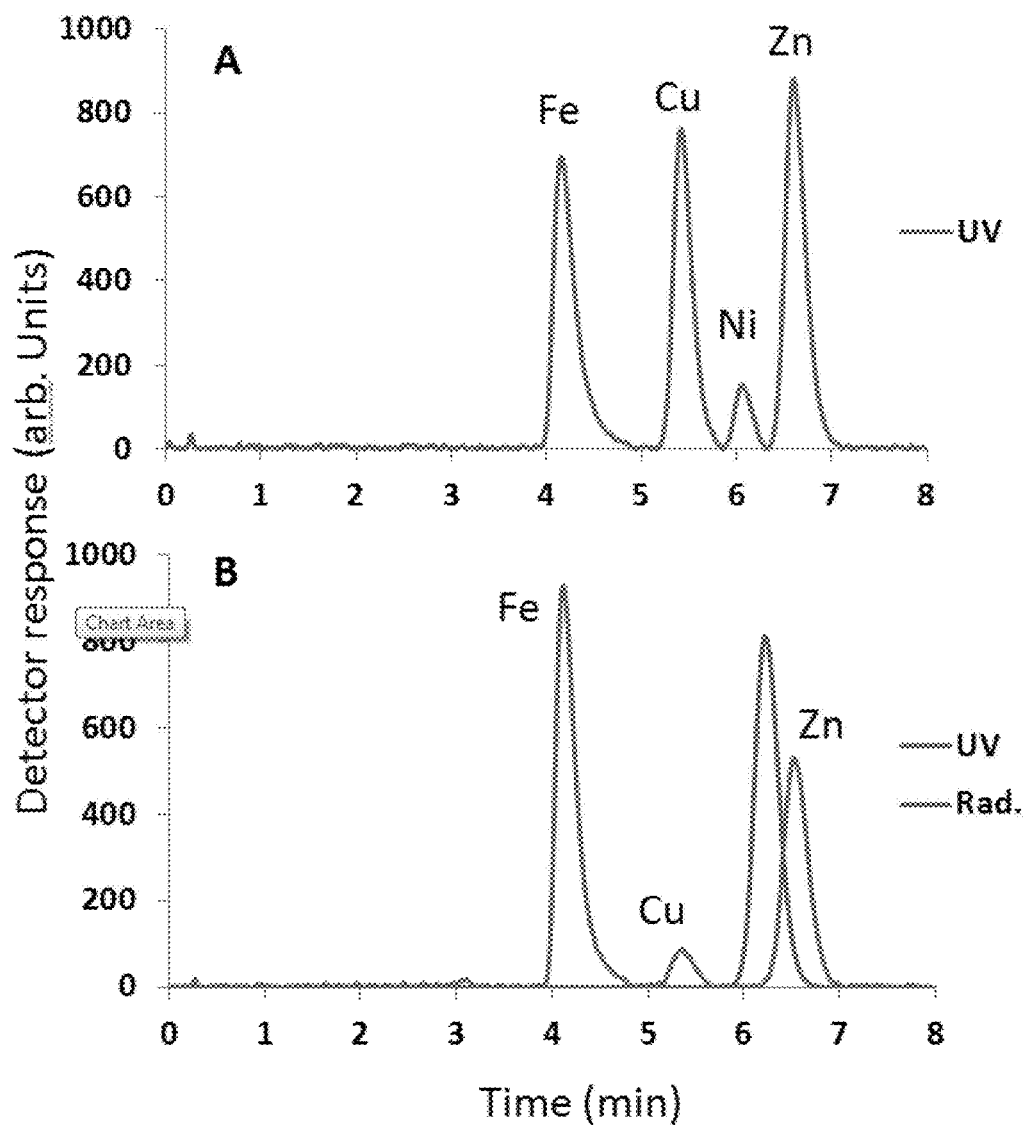
FIG. 6 shows Radio-HPLC chromatograms of cGMP $^{63}$Zn citrate product. A) UV chromatogram (530 nm) for reference standards for 2.5 mg/L each of $Fe^{+3}$, $Cu^{+2}$, $Ni^{+2}$, and $Zn^{+2}$. B) UV and radio-HPLC chromatograms for representative cGMP run of $^{63}$Zn citrate product. There is a 0.3 minute delay between the UV detector and the radioactivity detector.
Figure 7:
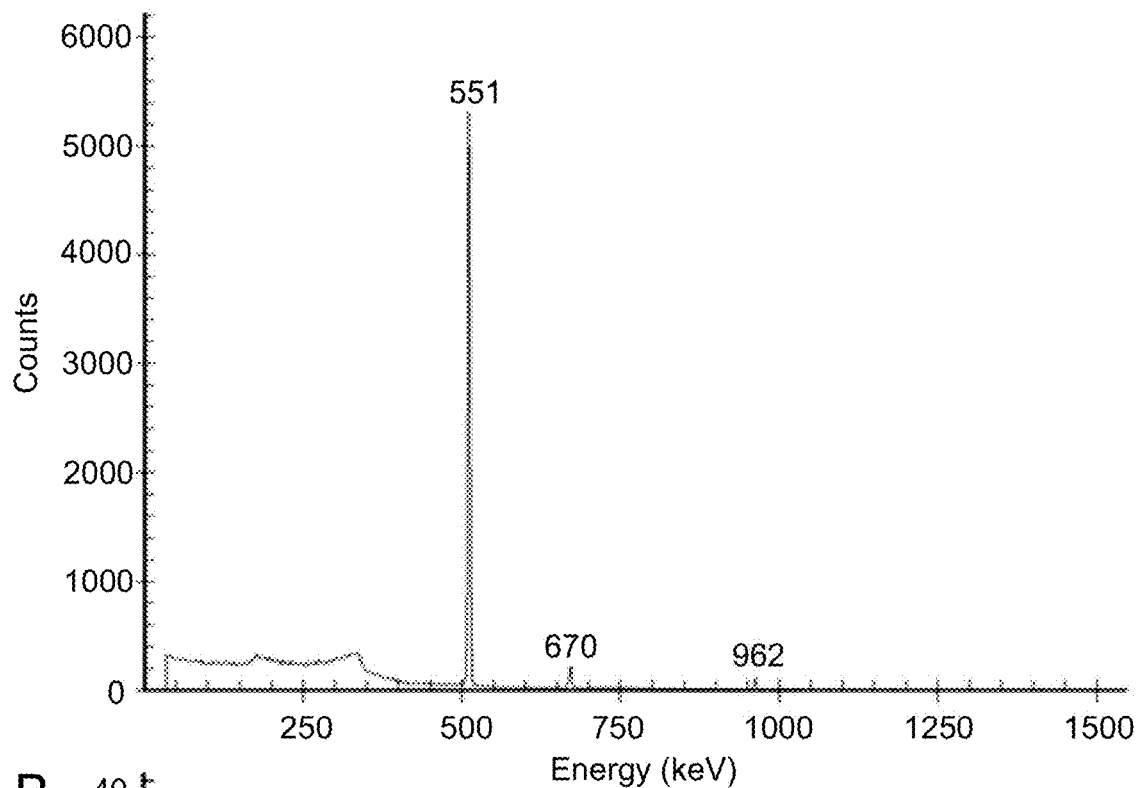
FIG. 7 shows high-purity Ge detector gamma spectrometry of $^{63}$Zn citrate product at A) 90 minutes after end of synthesis and B) 24 hours after end of synthesis.
Figure 7:
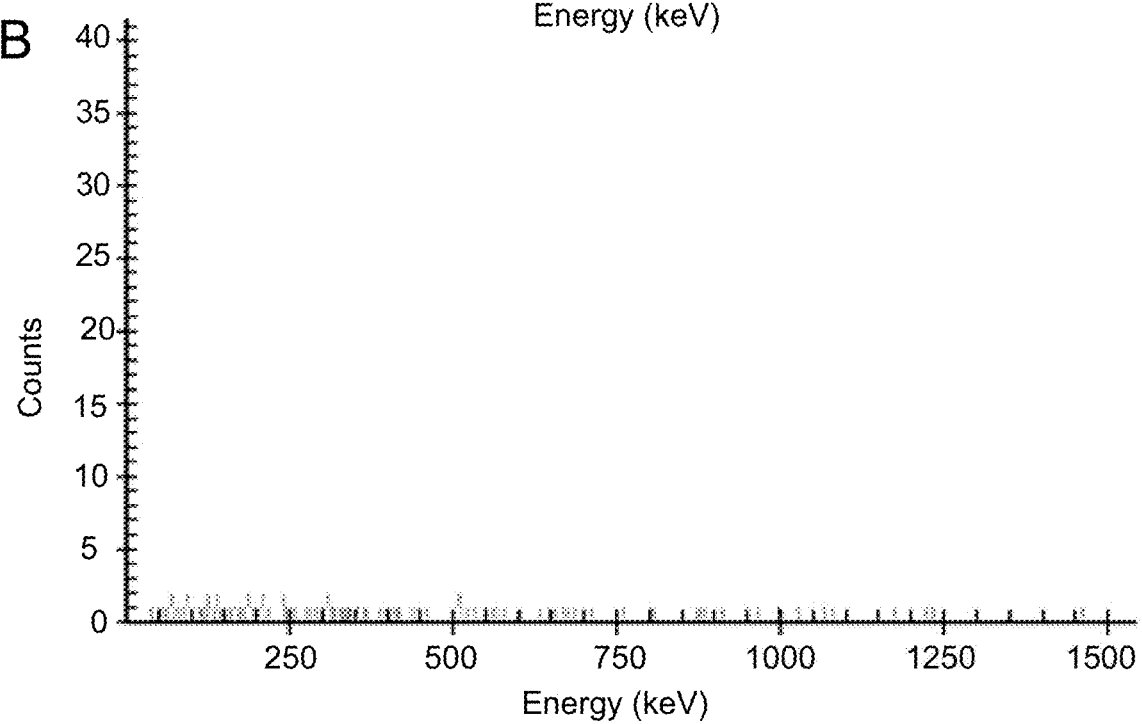

All standard radiopharmaceutical quality control tests were passed satisfactorily, including appearance, half-life (38.5±0.1 minutes), pH (6.5), endotoxins and sterility. Representative radio-HPLC chromatograms are shown in FIG. 6. A single radioactive peak at 6.3 minutes corresponded to the nonradioactive $Zn^{+2}$ retention time of 6.6 minutes, consistent with the time delay of 0.3 minutes between the radioactivity detector and the following UV detector. Analysis of metal ions in the product showed significant levels (2.6-40.5 μg per batch) of nonradioactive $Zn^{+2}$, $Cu^{+2}$, and $Fe^{+3}$. On the contrary, $Ni^{+2}$ was not detected in QC samples at a minimum detection level of ~1 μg/mL. It is important to note that copper levels were low, but significantly higher in the "non-cGMP" product as compared to the cGMP product (40.5±16.1 μg versus 2.6±1.8 μg) likely because the non-cGMP product was prepared using recycled AG resin that had retained small quantities of raw material $^{63}Cu$ that were subsequently released in later runs. In contrast, the iron levels were higher in the cGMP runs relative to the non-cGMP runs (37.4±1.6 versus 13.0±2.1). The greater use of disposable stainless steel needles during cGMP processing is likely responsible for the higher levels of iron in the cGMP runs. Radionuclide purity was found to be >99.9% by HP-Ge gamma spectrometry after end of synthesis with the known major emissions at 511 keV (185.5%), 670 keV (8.2%), and 962 keV (6.5%) (see FIG. 7A). There were no detectable gamma emissions above background remaining in the samples 24 hours after synthesis (see FIG. 7B). Specific activities of 34.2±13.8 MBq/μg (uncorrected) for the $^{63}Zn$ product were obtained. Thus, for a 370 MBq dose for a human study, approximately 11 μg (0.17 μmol) zinc would be administered. This level of zinc would represent a negligible amount compared to the plasma levels of zinc of approximately 10 μM (10).

Biodistribution in Normal Mice

The biodistribution at 1 hour showed the pancreas to have the highest SUV of 8.8±3.2, with high uptakes also seen in liver, kidney and upper intestine. Intestinal uptake likely reflected secretion of activity by the pancreas. Whole brain SUV was 0.24±0.09, showing significant retention in brain. The intracerebral regions did not show statistically significant differences in SUVs. Thus, brain uptake of $^{63}Zn$ was similar over the regions studied.

Discussion for Example 1

Potential applications for PET imaging of zinc dynamics in a broad spectrum of diseases (1-10) motivates the development of a practical method for producing $^{63}$Zn. Of the three known positron-emitting zinc isotopes, $^{63}$Zn has the most favorable properties for quantitative PET imaging in humans (see Table 3), although its 38.5 minute half-life will limit investigations to under 2-3 hours. Nevertheless, this time frame is sufficient to determine initial biodistribution patterns of zinc after intravenous injection, and fast to moderate tissue turnover times. The average positron energy of 0.992 MeV for $^{63}$Zn is significantly higher than that of $^{18}$F (0.25 MeV) but only slightly higher than $^{68}$Ga (0.84 MeV) and $^{124}$I (0.82 MeV). However, in comparison with $^{124}$I, the high-energy gamma emissions from $^{63}$Zn are benign (see Table 3). Thus, imaging spatial resolution is anticipated to be inferior to $^{18}$F, but on par with $^{68}$Ga.

As far as we are aware, this is the first reported method for producing radionuclidically pure $^{63}$Zn ion for use as a PET imaging probe. An earlier study by Guerra-Goméz produced $^{63}$Zn and small levels of $^{65}$Zn ($T_{1/2}$=244 d) contaminant after proton irradiation of natural copper foils. Since natural copper is comprised of 69.2% $^{63}$Cu and 30.8% $^{65}$Cu, enriched $^{63}$Cu is modestly expensive and readily available as a starting material for solution targetry. We are not aware of a commercial source of isotopically enriched $^{63}$Cu foil. Our method would be more practical because it eliminates the need for acid dissolution of the solid target before isotope separation. The yields of $^{63}$Zn citrate in our study (160-309 MBq) are sufficient to perform several human studies with the same batch (assuming multiple PET scanners are available simultaneously). Production yields can be increased by increasing the [$^{63}$Cu]copper nitrate concentration in the target solution and/or increasing irradiation time. We envision further improvement of the target design to enhance heat transfer that we anticipate will support higher beam currents.

The final chemical form of $^{63}$Zn in our method is zinc citrate, determined by the final elution of the CM cartridge with commercially available isotonic sodium citrate solution. $^{63}$Zn can also be eluted from the CM cartridge using an isotonic histidine chloride solution, but the elution efficiency is reduced. Another advantage of using an isotonic 4% sodium citrate solution is that a USP grade solution is commercially available for compliance with cGMP. We would assume that after entering the bloodstream, zinc would equilibrate among a number of potential binding agents, including serum albumin (15). Although albumin binds zinc with high affinity, the binding is characterized as exchangeable (16). Animal studies with $^{65}$Zn have shown rapid exchange of the blood and tissue compartments (17-19).

The initial evaluation of $^{63}$Zn citrate biodistribution in normal mice agrees with previous results with $^{65}$Zn in rats (19). Zinc is essential for the normal processing, storage, secretion, and action of insulin in pancreatic β-cells (20). The highest site of uptake of intravenously administered radiozinc is pancreas, where two $Zn^{+2}$ ions coordinate six molecules of insulin within the storage vesicles of β-cells (20). It is anticipated that $^{63}$Zn-PET may play an important role for noninvasive assessment of zinc turnover in pancreas in metabolic diseases, including metabolic syndrome, obesity and diabetes. The distribution into upper intestine at 60 minutes is likely due to pancreatic secretion of $^{63}$Zn into the upper gut.

Liver uptake is also prominent as liver is a highly metabolic organ that requires high levels of zinc associated with metabolic enzymes. As previously noted in other cancer types (4-6), hepatocellular carcinoma (HCC) tumors consistently show marked decreases in zinc concentration compared to normal liver (21), and thus zinc may serve as a biomarker for early identification of malignancy. Other potential applications in liver include monitoring of changes in liver zinc homeostasis in chronic active hepatitis and cirrhosis (ref: Gur G, Bayraktar Y, Ozer D, Ozdogan M, Kayhan B. Determination of hepatic zinc content in chronic liver disease due to hepatitis B virus. *Hepatogastroenterology.* 1998; 45:472-476.).

Finally, murine brain uptake of $^{63}$Zn was moderately low, but significant. Zinc is an important cofactor in neurotransmission in gamma-aminobutyric acid- (22), glutamate- (23), and glycine-mediated (24) processes. Kanayama et al. (25) showed that $^{65}$Zn uptake in rat brain at 30 minutes was several fold higher than any of the other metal ions measured (Be, Sc, V, Cr, Mn, Fe, Co, As, Se, Rb, Sr, Y, Zr, Tc, and Ru) demonstrating the robust transport of zinc across the blood-brain barrier. Interestingly, the same group showed markedly higher uptake of radioactive tracers of zinc, manganese and rubidium in intracerebral C6 glioma tumors (26). In addition to potential $^{63}$Zn-PET imaging applications in neurology and neurooncology, we anticipate imaging applications in Alzheimer's Disease (AD) and Huntington's Disease (HD). In these neurodegenerative diseases, a clear association has been made for zinc and copper metal ions in amyloid-β plaque formation and stabilization (7, 8). Amyloid-β protein is reversibly precipitated by zinc and copper and coordinates these metals in plaques (27). Intracerebral zinc levels are highly abnormal in AD: post-mortem analysis of brain samples in patients with AD showed that cortical zinc (but not copper) levels correlate with cognitive impairment (28). Metal chelator therapy directed at altering intracerebral zinc distribution is in active clinical investigation in AD (8), while zinc sulfate has been proposed as a therapy in HD (29). $^{63}$Zn-PET has potential to provide noninvasive monitoring of changes in zinc homeostasis in response to zinc related therapies.

TABLE 3

Positron-Emitting Isotopes Of Zinc

| Parent Nucleus | Decay Mode* | Daughter Nucleus | $T_{1/2}$ | Mean β⁺ energy MeV (total β⁺ intensity) | High-energy Emissions MeV (Intensity %) |
|---|---|---|---|---|---|
| $^{62}$Zn | EC, β⁺ | $^{62}$Cu ($T_{1/2}$ = 9.7 m) | 9.26 h | 0.259 (8.4) | 0.508 (15%), 0.55 (15%), 0.60 (26%) |
| $^{63}$Zn | EC, β⁺ | $^{63}$Cu (stable) | 38.47 m | 0.992 (92.7) | 0.67 (8%), 0.96 (7%) |
| $^{65}$Zn | EC, β⁺ | $^{65}$Cu (stable) | 243.9 d | 0.1425 (1.42) | 1.11 (50.6%) |

*Electron capture

TABLE 4

Production Yield, Specific Activity And Metal Impurities In $^{63}$Zn Citrate Preparations

| Group | $^{63}$Cu Used (mg/batch) | Conc. Of $^{63}$Cu(NO$_3$)$_2$ (M) | Batch yield after process* (GBq) | Saturated yield after process** (MBq/μA) | Specific Activity‡ (MBq/μg) | Metals (μg) |
|---|---|---|---|---|---|---|
| Non-cGMP | 321 (n = 3) | 1.7 | 3.06 ± 0.16 | 309 ± 17 | 108 ± 62 (36-144) | $Fe^{+3}$: 13.0 ± 2.1<br>$Cu^{+2}$: 40.5 ± 16.1<br>$Ni^{+2}$: n.d.<br>$Zn^{+2}$: 16.1 ± 8.3 |
| cGMP | 232 (n = 3) | 1.23 | 1.88 ± 0.44 | 160 ± 17 | 34.2 ± 13.8 (19.2-46.5) | $Fe^{+3}$: 37.4 ± 1.6 £<br>$Cu^{+2}$: 2.6 ± 1.8 £<br>$Ni^{+2}$: n.d.<br>$Zn^{+2}$: 25.2 ± 1.4 |

All irradiations were at beam current of 20 μA for 60 minutes
*decay corrected to EOB, processing time was ~36 minutes
**decay corrected to EOB
‡At end of synthesis
Non-cGMP process, reused AG50W-X8 resin
GMP process, new AG50W-X8 resin
£ p < 0.05 versus

TABLE 5

Biodistribution of $^{63}$Zn citrate in normal mice (n = 4) at 1 hour after IV administration

| Tissue | SUV |
|---|---|
| Blood | 0.57 ± 0.25 |
| Heart | 1.12 ± 0.23 |
| Lung | 2.06 ± 0.62 |
| Liver | 5.97 ± 1.92 |
| Pancreas | 8.78 ± 3.22 |
| Kidney | 4.21 ± 1.30 |
| Upper Intestine | 4.72 ± 2.18 |
| Muscle | 0.21 ± 0.08 |
| Bone | 0.76 ± 0.34 |
| Spleen | 2.30 ± 1.01 |
| Prostate | 0.58 ± 0.23 |
| Seminal vesicle | 1.69 ± 0.79 |
| Whole brain | 0.24 ± 0.09 |
| Cortex | 0.19 ± 0.07 |
| Caudate nuclei | 0.37 ± 0.23 |
| Hippocampus | 0.48 ± 0.37 |
| Thalamus | 0.26 ± 0.10 |
| Brain stem | 0.25 ± 0.09 |
| Cerebellum | 0.31 ± 0.14 |

Conclusion for Example 1

A production method has been developed for the first time for radionuclidically pure $^{63}$Zn based on solution target methods. The radiopharmaceutical preparation has been successfully tested according to standard cGMP quality control tests. Uncorrected yields of 933±222 MBq were obtained using a 1.23 M $^{63}$Cu nitrate solution and proton irradiation at 20 μA for 60 minutes. This amount is sufficient for 2-3 doses of $^{63}$Zn for human studies (~370 MBq/dose). If greater quantities of $^{63}$Zn are needed, production levels can be readily increased by increasing the $^{63}$Cu nitrate concentration and/or increasing irradiation time. Specific activity is sufficient not to significantly increase zinc levels in the blood in animal and human studies. In conclusion, a practical and efficient method of production of $^{63}$Zn citrate has been developed that will enable PET imaging studies of zinc biodisposition and kinetics in animal and human studies.

References for Example 1

1. Frassinetti S, Bronzetti G, Caltavuturo L, Cini M, Croce C D. The role of zinc in life: a review. *J Environ Pathol Toxicol Oncol.* 2006; 25(3):597-610.
2. Penny M E. Zinc supplementation in public health. *Ann Nutr Metab.* 2013; 62 Suppl 1:31-42.
3. Miao X, Sun W, Fu Y, Miao L, Cai L. Zinc homeostasis in the metabolic syndrome and diabetes. Front Med. March 2013; 7(1):31-52.
4. Costello L C, Levy B A, Desouki M M, et al. Decreased zinc and downregulation of ZIP3 zinc uptake transporter in the development of pancreatic adenocarcinoma. *Cancer Biol Ther.* Aug. 15 2011; 12(4):297-303.
5. Kolenko V, Teper E, Kutikov A, Uzzo R. Zinc and zinc transporters in prostate carcinogenesis. *Nat Rev Urol* April 2013; 10(4):219-226.
6. Alam S, Kelleher S L. Cellular mechanisms of zinc dysregulation: a perspective on zinc homeostasis as an etiological factor in the development and progression of breast cancer. *Nutrients.* August 2012; 4(8):875-903.
7. Craddock T J, Tuszynski J A, Chopra D, et al. The zinc dyshomeostasis hypothesis of Alzheimer's disease. *PLoS One.* 2012; 7(3):e33552.
8. Lannfelt L, Blennow K, Zetterberg H, et al. Safety, efficacy, and biomarker findings of PBT2 in targeting Abeta as a modifying therapy for Alzheimer's disease: a phase IIa, double-blind, randomised, placebo-controlled trial. *Lancet NeuroL September* 2008; 7(9):779-786.
9. Fujibayashi Y, Saji H, Kawai K, et al. A radiopharmaceutical for pancreatic exocrine functional diagnosis: $^{62}$Zn-EDDA metabolism in pancreas. *Int J Nucl Med Biol.* 1986; 12(6):447-451.
10. Takeda A. Movement of zinc and its functional significance in the brain. *Brain Res Brain Res Rev.* December 2000; 34(3):137-148.
11. Lyster D M, Noujaim A A. The unit dose preparation of $^{63}$Zn-EDTA for use in nuclear medicine. *Int J Nucl Med Biol.* June 1974; 1(4):220-223.
12. Guerra-Gomez F L G, Takada Y, Hosoi R, et al. Production and purification of the positron emitter zinc-63. *J Labelled Compd Rad.* January 2012; 55(1):5-9.
13. Pandey M K, Engelbrecht H P, Byrne J P, Packard A B, Degrado T R. Production of $^{89}$Zr via the $^{89}$Y(p,n)$^{89}$Zr reaction in aqueous solution: Effect of solution composition on in-target chemistry. *Nucl Med Biol*. April 2014; 41(4): 309-316.

14. Pandey M, Byrne J, Jiang H, A B P, DeGrado T. Cyclotron production of 68Ga via the $^{68}$Zn(p,n)$^{68}$Ga reaction in aqueous solution. *American Journal of Nuclear Medicine and Molecular Imaging*. in press.

15. Blindauer C A, Harvey I, Bunyan K E, et al. Structure, properties, and engineering of the major zinc binding site on human albumin. *J Biol Chem*. Aug. 21, 2009; 284(34): 23116-23124.

16. Lu J, Stewart A J, Sadler P J, Pinheiro T J, Blindauer C A. Albumin as a zinc carrier: properties of its high-affinity zinc-binding site. *Biochem Soc Trans*. December 2008; 36(Pt 6):1317-1321.

17. Tibaduiza E C, Bobilya D J. Zinc transport across an endothelium includes vesicular cotransport with albumin. *J Cell Physiol*. June 1996; 167(3):539-547.

18. Buxani-Rice S, Ueda F, Bradbury M W. Transport of zinc-65 at the blood-brain barrier during short cerebrovascular perfusion in the rat: its enhancement by histidine. *J Neurochem*. February 1994; 62(2):665-672.

19. Pullen R G, Franklin P A, Hall G H. $^{63}$zinc uptake from blood into brain and other tissues in the rat. Neurochem Res. October 1990; 15(10):1003-1008.

20. Li Y V. Zinc and insulin in pancreatic beta-cells. Endocrine. March 2014; 45(2):178-189.

21. Costello L C, Franklin R B. The status of zinc in the development of hepatocellular cancer: An important, but neglected, clinically established relationship. *Cancer Biol Ther*. Jan. 21, 2014; 15(4).

22. Cohen-Kfir E, Lee W, Eskandari S, Nelson N. Zinc inhibition of gamma-aminobutyric acid transporter 4 (GAT4) reveals a link between excitatory and inhibitory neurotransmission. *Proc Natl Acad Sci USA*. Apr. 26, 2005; 102(17):6154-6159.

23. Nutini M, Frazzini V, Marini C, Spalloni A, Sensi S L, Longone P. Zinc pre-treatment enhances NMDAR-mediated excitotoxicity in cultured cortical neurons from SOD1 (G93A) mouse, a model of amyotrophic lateral sclerosis. *Neuropharmacology*. June 2011; 60(7-8):1200-1208.

24. Laube B. Potentiation of inhibitory glycinergic neurotransmission by $Zn^{2+}$: a synergistic interplay between presynaptic P2X2 and postsynaptic glycine receptors. *Eur J Neurosci*. September 2002; 16(6):1025-1036.

25. Kanayama Y, Tsuji T, Enomoto S, Amano R. Multi-tracer screening: brain delivery of trace elements by eight different administration methods. *Biometals*. December 2005; 18(6):553-565.

26. Tamano H, Enomoto S, Oku N, Takeda A. Preferential uptake of zinc, manganese, and rubidium in rat brain tumor. *Nucl Med Biol*. May 2002; 29(4):505-508.

27. Adlard P A, Bush A I. Metals and Alzheimer's disease. *J Alzheimers Dis*. November 2006; 10(2-3):145-163.

28. Religa D, Strozyk D, Cherny R A, et al. Elevated cortical zinc in Alzheimer disease. *Neurology*. Jul. 11, 2006; 67(1):69-75.

29. Wu C L. Zinc sulfate could be a potential agent for the treatment of. Huntington's disease through activating central TrkB signaling. *CNS Spectr*. January 2010; 15(1):56-57.

Example 2

Data from human subjects is shown in FIGS. 8-12.

Figure 8:
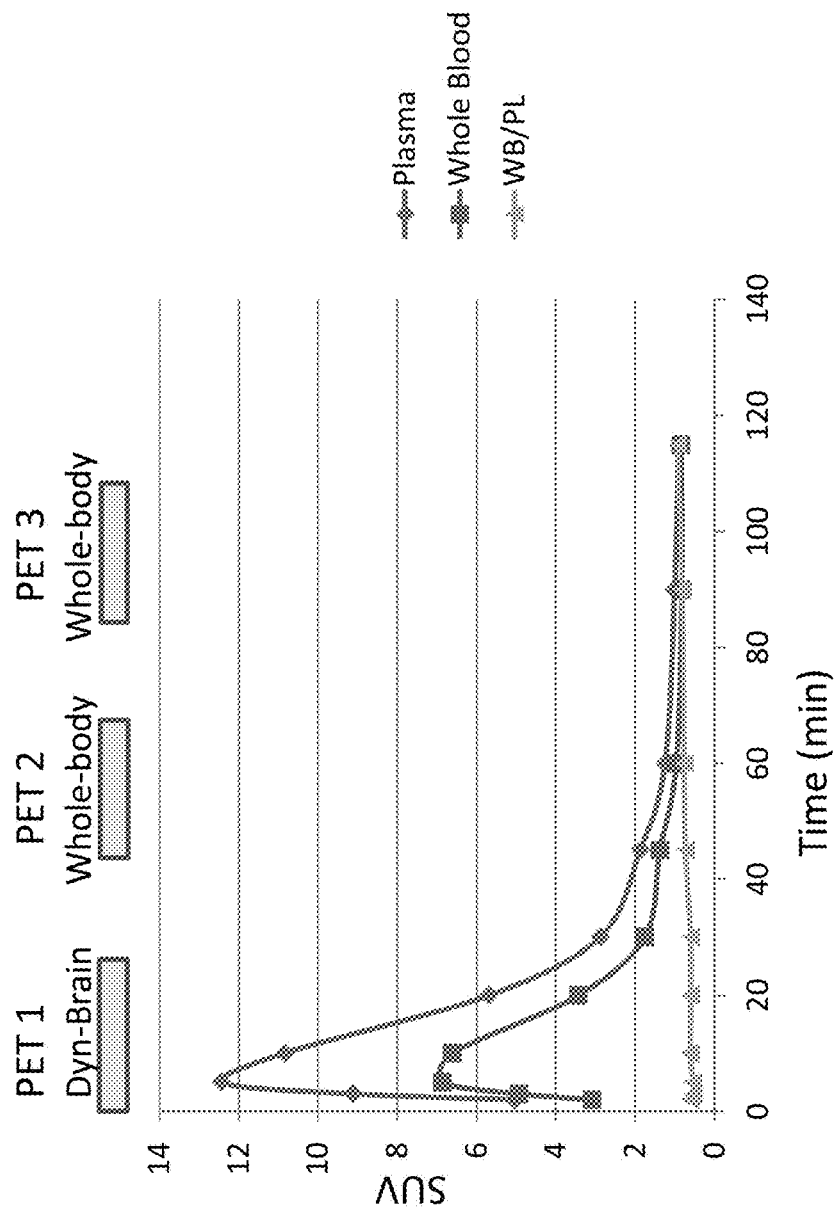
FIG. 8 shows pharmacokinetics of $^{63}$Zn Citrate in an Alzheimer's disease patient.

FIG. 8 shows the pharmacokinetics of $^{63}$Zn Citrate in an Alzheimer's disease patient. Venous blood samples were taken in heparinized tubes after injection of radiotracer. The samples were centrifuged, and plasma separated. The curves show a rapid clearance of $^{63}$Zn from the blood that is completed by 90 minutes. After this time, the concentrations of $^{63}$Zn in both plasma and whole blood are relatively constant. The concentration of $^{63}$Zn in whole-blood rises relative to plasma to reach equilibrium at around 90 minutes post-injection.

Figure 9:
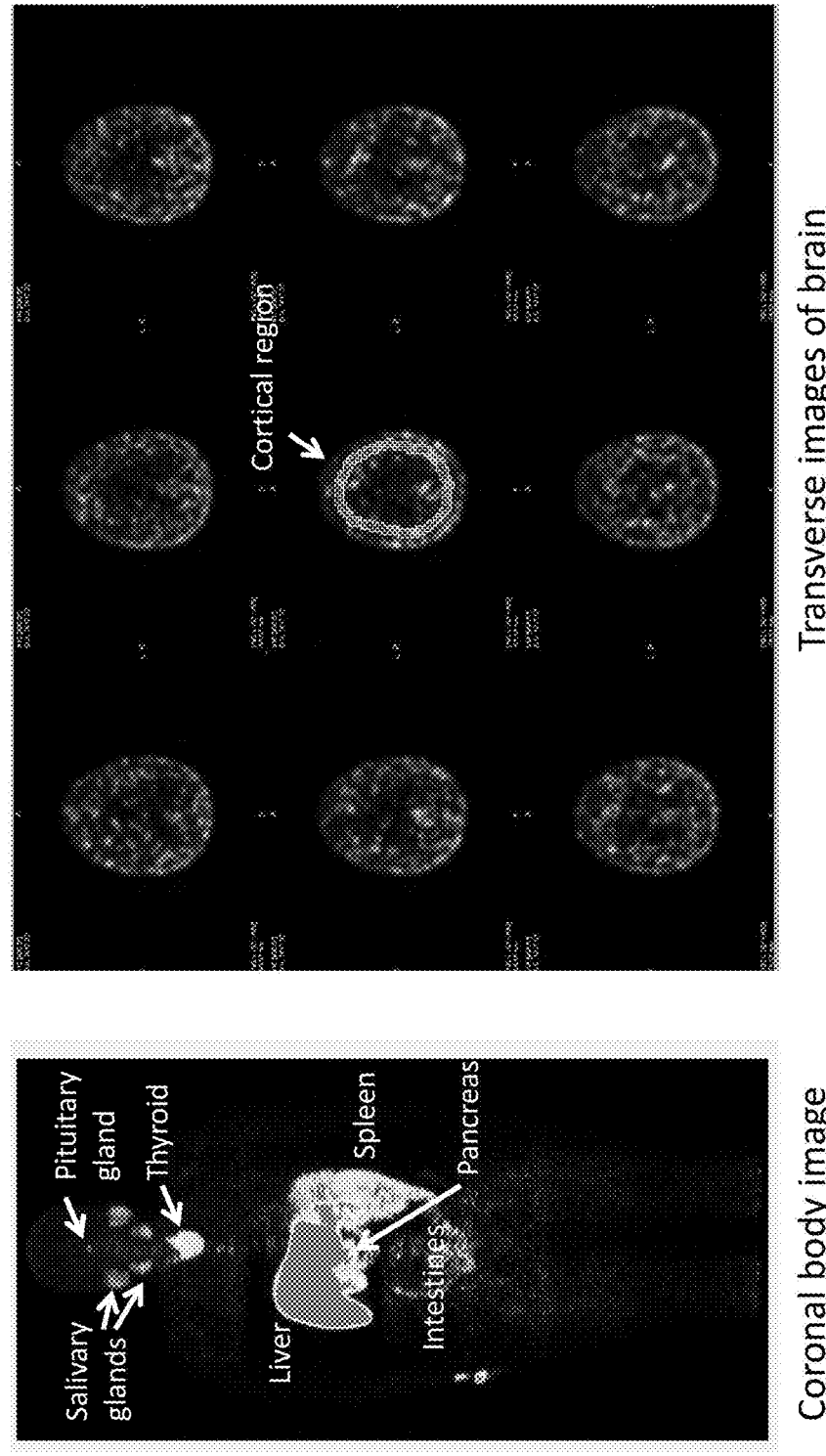
FIG. 9 shows PET images of $^{63}$Zn Citrate in a female healthy human subject.

FIG. 9 shows PET images of $^{63}$Zn Citrate in a female healthy elderly (64 years) human subject. High uptake is seen in liver, pancreas, spleen, intestines, and thyroid. Moderate to low uptake is seen in cerebral cortex, pituitary gland, and salivary glands.

Figure 10:
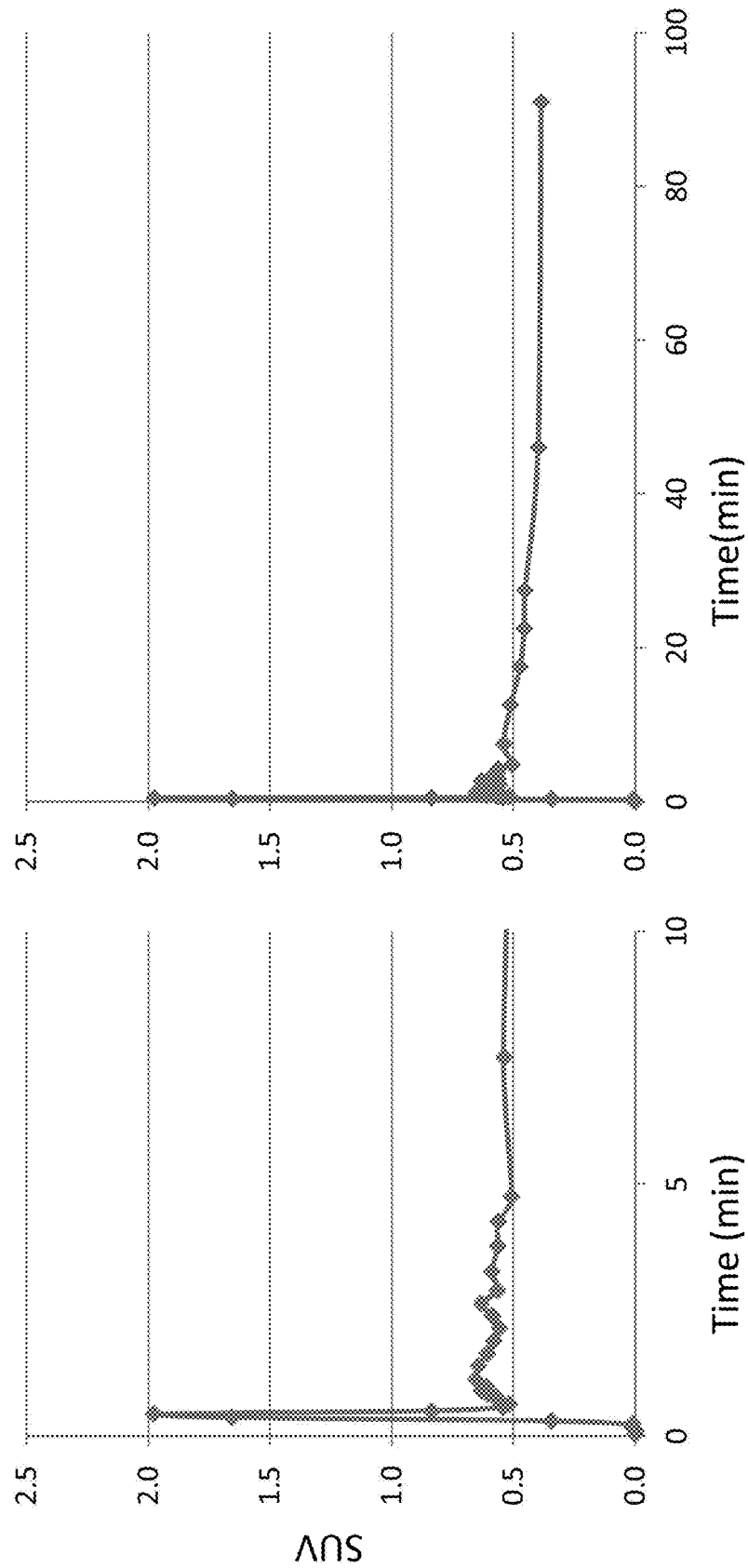
FIG. 10 shows pharmacokinetics of $^{63}$Zn Citrate in cerebral cortical region of interest in a healthy elderly subject.

FIG. 10 shows the pharmacokinetics of $^{63}$Zn Citrate in cerebral cortical region of interest in an healthy elderly subject. The curves show a rapid vascular clearance phase in the first minute post-injection. After this time, there is slower clearance from the cortical brain region, with little clearance between 50 minutes and 90 minutes.

Figure 11:
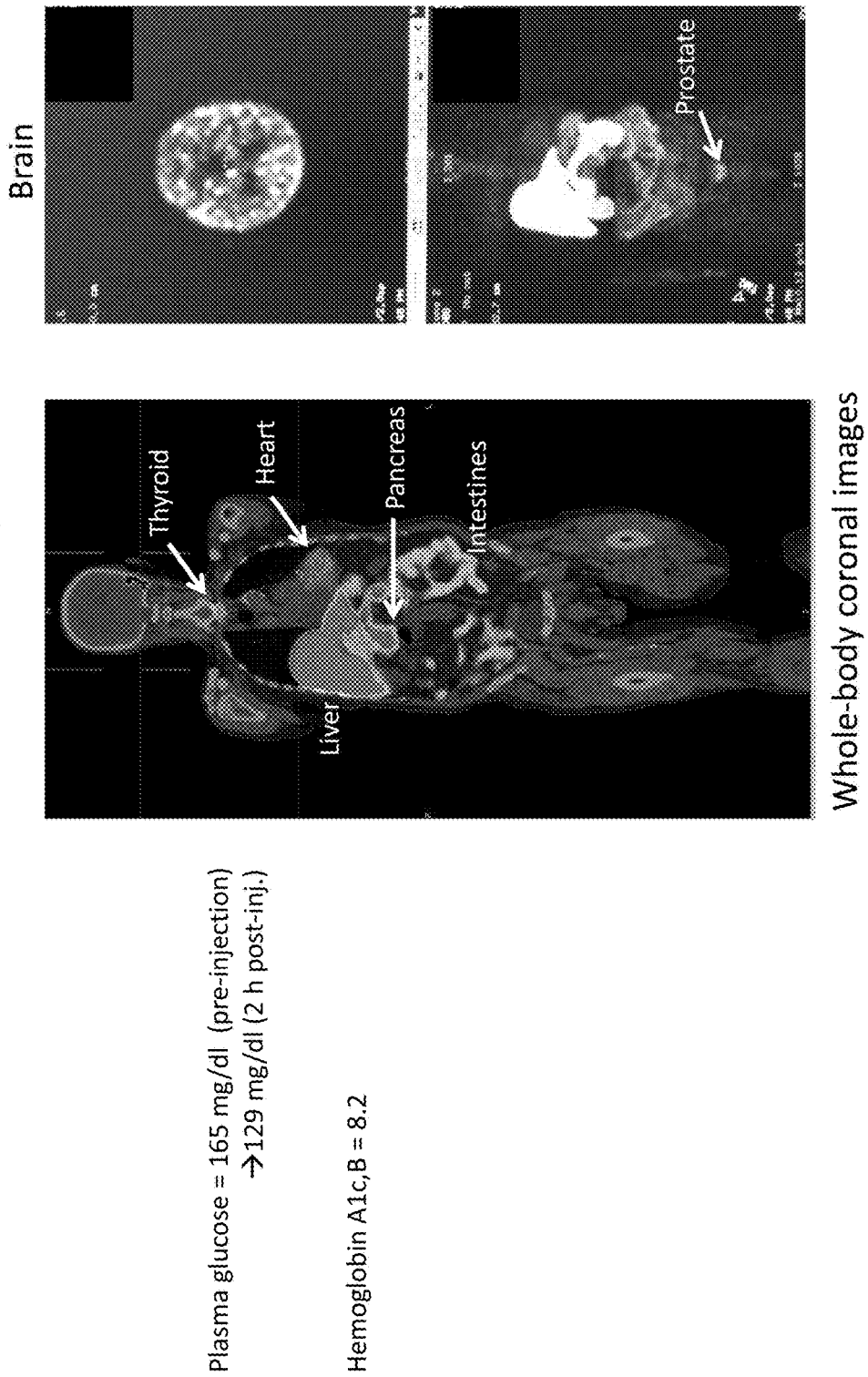
FIG. 11 shows PET images of $^{63}$Zn Citrate in a male Alzheimer's disease subject.

FIG. 11 shows PET images of $^{63}$Zn Citrate in a male Alzheimer's disease subject (78 years). High uptake is seen in liver, pancreas, spleen, intestines, and thyroid. Moderate to low uptake is seen in cerebral cortex, prostate, pituitary gland, and salivary glands.

Figure 12:
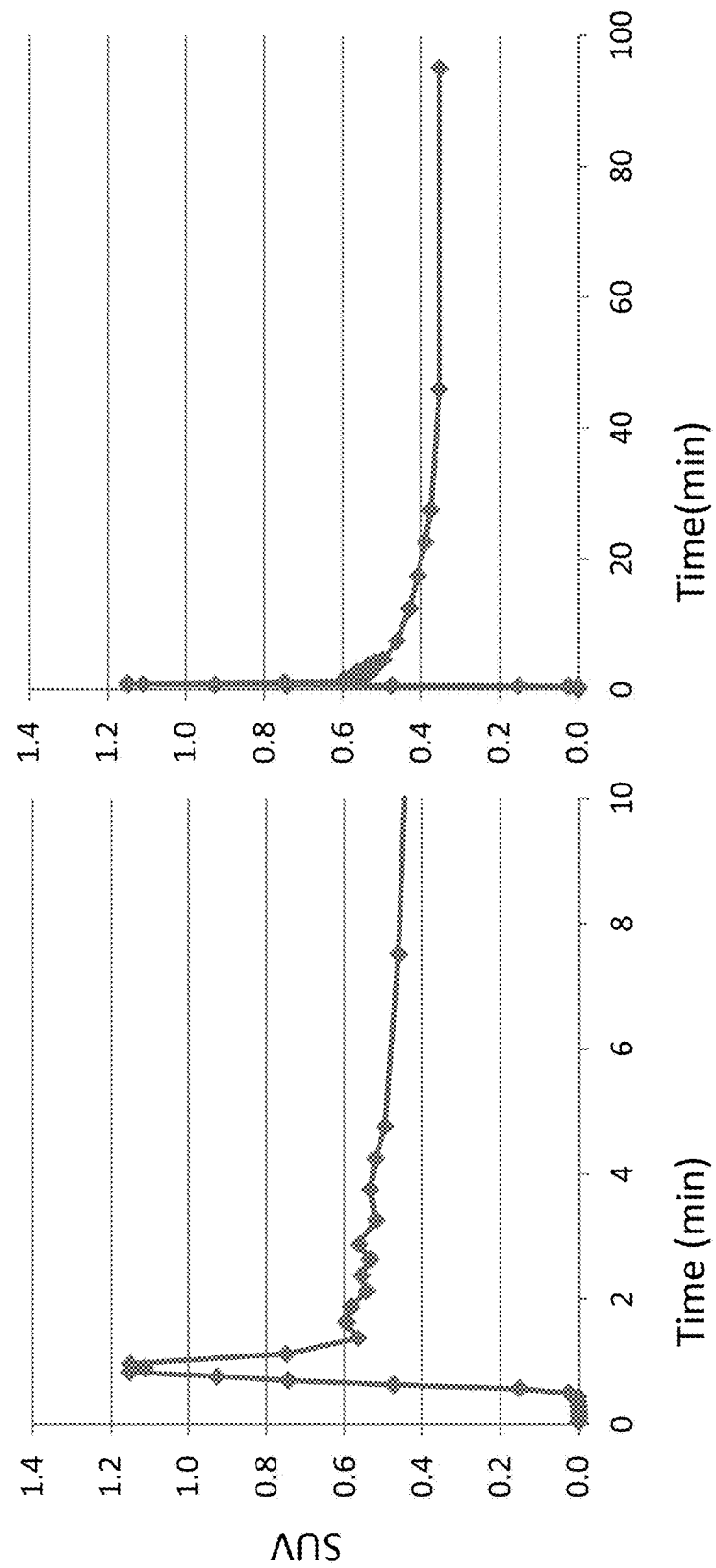
FIG. 12 shows pharmacokinetics of $^{63}$Zn Citrate in cerebral cortical region of interest in a subject with Alzheimer's disease.

FIG. 12 shows the pharmacokinetics of $^{63}$Zn Citrate in cerebral cortical region of interest in a subject with Alzheimer's disease (78 years). The curves show a rapid vascular clearance phase in the first minute post-injection. After this time, there is slower clearance from the cortical brain region, with little clearance between 50 minutes and 90 minutes.

The techniques of Example 2 can be used in a method for detecting or ruling out Alzheimer's disease in a patient. For example, a detectable amount of $^{63}$Zn citrate can be administered to a patient wherein the $^{63}$Zn is targeted to β-amyloid in the patient. One acquires an image using positron emission tomography to detect the presence or absence of $^{63}$Zn binding to β-amyloid in the patient. The image can be compared to a reference image to determine if the patient has an increased amount of β-amyloid compared to the reference image. The reference image can be a control image of a control subject such as in FIG. 9, wherein the control subject has normal cognitive function. Alternatively, the reference image can be a baseline image from a prior scan of the patient's brain, in which case progression of Alzheimer's disease could be determined.

The techniques of Example 2 can also be used in a method for detecting or ruling out cancer in a patient. Abnormally low zinc levels can be implicated in various cancers, such as prostate cancer, pancreatic cancer, or liver cancer. A detectable amount of $^{63}$Zn citrate can be administered to a patient wherein the $^{63}$Zn is targeted to tissue (e.g., prostate, pancreas, or liver) in the patient. One acquires an image using positron emission tomography to detect $^{63}$Zn binding to tissue in the patient. The image can be compared to a reference image to determine if the patient has a decreased amount of zinc uptake in the tissue compared to the reference image. The reference image can be a control image of a control subject such as in FIG. 9, wherein the control subject has normal function. Alternatively, the reference image can be a baseline image from a prior scan of the patient's tissue, in which case, progression of cancer could be determined. For conditions in which decreased zinc transporter function may be indicated, $^{63}$Zn may be associated (e.g., via ionic or covalent bonding) with a complex that binds a protein having a zinc transporter function. Differences in the PET image and the reference image in the region of interest may indicate decreased uptake of the protein binding complex in the region of interest. This may indicate decreased zinc transporter function in the tissue in the region of interest.

Thus, the present invention provides a positron emitting zinc cation of $^{63}$Zn useful in PET imaging of biological systems for noninvasive measurement of zinc transport and zinc biodistribution.

The present invention has been described in terms of one or more example embodiments, and it should be appreciated that many equivalents, alternatives, variations, and modifications, aside from those expressly stated, are possible and within the scope of the invention.

The invention claimed is:

1. A method for detecting zinc distribution in a patient, the method comprising:
    (a) administering to a patient a detectable amount of a pharmaceutically acceptable compound including a zinc cation and a citrate anion, wherein the zinc cation is a $^{63}$Zn positron emitter; and
    (b) acquiring an image using a medical imaging technique to detect the distribution of zinc in the patient.

2. The method of claim 1 wherein the medical imaging technique is positron emission tomography.

3. The method of claim 1 wherein the $^{63}$Zn is associated with a complex that binds a protein having a zinc transporter function.

4. The method of claim 1 wherein the zinc cation is targeted to tissue in a region of interest in the patient.

5. The method of claim 4 wherein:
the region of interest is the patient's brain.

6. The method of claim 4 wherein:
the region of interest is the patient's prostate.

7. The method of claim 4 wherein:
the region of interest is the patient's liver.

8. The method of claim 4 wherein:
the region of interest is the patient's pancreas.

9. The method of claim 4 further comprising:
    (c) comparing the image to a reference image to determine if the patient has a decreased amount of zinc uptake in the tissue compared to the reference image.

10. The method of claim 9, wherein the reference image is a control image of a control region of interest of a control subject.

11. The method of claim 9, wherein the reference image is a baseline image from a prior scan of the region of interest of the patient.

12. The method of claim 9 wherein:
the $^{63}$Zn is associated with a complex that binds a protein having a zinc transporter function, and
differences in the image and the reference image indicate decreased uptake of the complex in the tissue.

13. The method of claim 9 wherein:
the $^{63}$Zn is associated with a complex that binds a protein having a zinc transporter function, and
differences in the image and the reference image indicate decreased zinc transporter function in the tissue.

14. The method of claim 9 wherein:
the reference image is a control image of a control subject, and
the control subject has normal cognitive function.

* * * * *

UNITED STATES PATENT AND TRADEMARK OFFICE
CERTIFICATE OF CORRECTION

PATENT NO. : 11,103,602 B2
APPLICATION NO. : 16/355335
DATED : August 31, 2021
INVENTOR(S) : Timothy R. Degrado et al.

It is certified that error appears in the above-identified patent and that said Letters Patent is hereby corrected as shown below:

In the Specification

Column 2, Line 26, "(Aβ)" should be --(AβO)--.

Column 2, Lines 32-33, "Jul 10:59(443-55" should be --Jul 10:59(1):43-55--.

Column 8, Line 46, "Hz" should be --$H_2$--.

Column 8, Line 50, "Hz" should be --$H_2$--.

Column 15, Line 3, "26 zn" should be --$^{62}Zn$--.

Column 15, Line 26, "natCu(p,n)$^{63}$Zn" should be --$^{nat}Cu(p,n)^{63}Zn$--.

Column 17, Line 18, "CSSA" should be --C5SA--.

Column 19, Line 11, "and $^{124}$1" should be --and $^{124}I$--.

Column 19, Line 11, "with $^{124}$1" should be --with $^{124}I$--.

Column 22, Line 38, "UroL" should be --Urol.--.

Column 22, Line 51, "NeuroL" should be --Neurol.--.

Signed and Sealed this
Twenty-fifth Day of January, 2022

Drew Hirshfeld
*Performing the Functions and Duties of the
Under Secretary of Commerce for Intellectual Property and
Director of the United States Patent and Trademark Office*